(12) United States Patent
Hasilo et al.

(10) Patent No.: US 10,034,963 B2
(45) Date of Patent: Jul. 31, 2018

(54) METHODS AND DEVICES FOR CELLULAR TRANSPLANTATION

(71) Applicant: Sernova Corporation, London (CA)

(72) Inventors: Craig Hasilo, Montreal (CA); Justin Leushner, London (CA); Daniel Nicholas Haworth, Marlborough (GB); Simon Shohet, Potton (GB); Philip Michael Toleikis, Vancouver (CA); Delfina Maria Mazzuca Siroen, London (CA)

(73) Assignee: Sernova Corporation, London, Ontario (CA)

( * ) Notice: Subject to any disclaimer, the term of this patent is extended or adjusted under 35 U.S.C. 154(b) by 7 days.

(21) Appl. No.: 14/993,416

(22) Filed: Jan. 12, 2016

(65) Prior Publication Data

US 2016/0151541 A1    Jun. 2, 2016

Related U.S. Application Data

(63) Continuation of application No. 14/625,135, filed on Feb. 18, 2015, which is a continuation of application
(Continued)

(51) Int. Cl.
*A61L 27/38* (2006.01)
*A61F 2/02* (2006.01)
(Continued)

(52) U.S. Cl.
CPC .......... *A61L 27/3886* (2013.01); *A61F 2/022* (2013.01); *A61L 27/16* (2013.01);
(Continued)

(58) Field of Classification Search
CPC ... A61F 2/022; C12N 5/0677; C12N 2533/30; A61L 27/3804; A61L 27/3834;
(Continued)

(56) References Cited

U.S. PATENT DOCUMENTS 3,866,609 A    2/1975   Sparks
5,620,883 A    4/1997   Shao et al.
(Continued)

FOREIGN PATENT DOCUMENTS

EP    0 773 753 B1    10/2003
EP    1 454 641 A2     9/2004
(Continued)

OTHER PUBLICATIONS

Cheung et al. Natural fibre-reinforced composites for bioengineering and environmental engineering applications. Composites: Part B (2009), v40, p. 655-663. (Year: 2009).*
(Continued)

*Primary Examiner* — Sean C. Barron
(74) *Attorney, Agent, or Firm* — Finnegan, Henderson, Farabow, Garrett & Dunner, LLP

(57) ABSTRACT

Devices and methods for transplanting cells in a host body are described. The cell comprises a porous scaffold that allows ingrowth of vascular and connective tissues, a plug or plug system configured for placement within the porous scaffold, and a seal configured to enclose a proximal opening in the porous scaffold. The device may further comprise a cell delivery device for delivering cells into the porous scaffold. The method of cell transplantation comprises a two step process. The device is incubated in the host body to form a vascularized collagen matrix around a plug positioned within the porous scaffold. The plug is then retracted from the porous scaffold, and cells are delivered into the vascularized space created within the porous scaffold.

23 Claims, 21 Drawing Sheets

Related U.S. Application Data

No. 13/393,038, filed as application No. PCT/US2010/047028 on Aug. 27, 2010, now Pat. No. 9,011,899.

(60) Provisional application No. 61/238,011, filed on Aug. 28, 2009.

(51) Int. Cl.

| | | |
|---|---|---|
| *A61L 27/58* | (2006.01) | |
| *A61M 39/02* | (2006.01) | |
| *A61L 27/54* | (2006.01) | |
| *A61L 27/16* | (2006.01) | |
| *A61L 27/56* | (2006.01) | |
| *C12N 5/071* | (2010.01) | |
| *A61K 35/12* | (2015.01) | |

(52) U.S. Cl.
CPC ....... *A61L 27/3804* (2013.01); *A61L 27/3834* (2013.01); *A61L 27/54* (2013.01); *A61L 27/56* (2013.01); *A61L 27/58* (2013.01); *A61M 39/0247* (2013.01); *C12N 5/0677* (2013.01); *A61K 35/12* (2013.01); *A61L 2300/64* (2013.01); *A61L 2400/18* (2013.01); *A61L 2420/00* (2013.01); *A61M 2039/0282* (2013.01); *C12N 2533/30* (2013.01)

(58) Field of Classification Search
CPC .......... A61L 27/56; A61L 27/16; A61L 27/54; A61L 27/58; A61L 27/3886; A61L 2400/18; A61L 2300/64; A61L 2420/00; A61M 39/0247; A61M 2039/0282; C08L 23/12; A61K 35/12
See application file for complete search history.

(56) References Cited

U.S. PATENT DOCUMENTS

| | | |
|---|---|---|
| 5,653,688 A | 8/1997 | Mills et al. |
| 5,686,091 A | 11/1997 | Leong et al. |
| 5,725,854 A | 3/1998 | Selawry |
| 5,733,336 A | 3/1998 | Neuenfeldt et al. |
| 5,741,334 A | 4/1998 | Mullon et al. |
| 5,759,534 A | 6/1998 | Selawry |
| 5,776,747 A | 7/1998 | Schinstine et al. |
| 5,843,069 A | 12/1998 | Butler et al. |
| 5,843,430 A | 12/1998 | Selawry |
| 5,849,285 A | 12/1998 | Selawry |
| 5,881,733 A | 3/1999 | Stone |
| 5,958,404 A | 9/1999 | Selawry |
| 5,964,261 A | 10/1999 | Neuenfeldt et al. |
| 6,149,907 A | 11/2000 | Selawry |
| 6,479,066 B1 | 11/2002 | Harpstead |
| 6,716,246 B1 | 4/2004 | Gonzalez |
| 7,399,751 B2 | 7/2008 | Kirkpatrick et al. |
| 2002/0065553 A1 | 5/2002 | Weber |
| 2002/0155559 A1 | 10/2002 | Laurencin et al. |
| 2004/0014212 A1 | 1/2004 | Elliott et al. |
| 2005/0070883 A1 | 3/2005 | Brown et al. |
| 2005/0118145 A1 | 6/2005 | Dufour et al. |
| 2006/0263406 A1 | 11/2006 | Lyles et al. |
| 2008/0026455 A1 | 1/2008 | Liao et al. |
| 2008/0145348 A1 | 6/2008 | Kirkpatrick et al. |
| 2009/0162331 A1 | 6/2009 | Dufour et al. |
| 2009/0191167 A1 | 7/2009 | White |
| 2012/0252045 A1 | 10/2012 | Pepper |
| 2016/0082158 A1 | 3/2016 | Shapiro |

FOREIGN PATENT DOCUMENTS

| | | |
|---|---|---|
| JP | 2003-524451 | 8/2003 |
| JP | 2010-517621 | 5/2010 |
| RU | 2240755 C2 | 3/2004 |
| WO | WO 93/08850 A1 | 5/1993 |
| WO | WO 94/08702 A1 | 4/1994 |
| WO | WO 95/18583 A1 | 7/1995 |
| WO | WO 95/28167 A1 | 10/1995 |
| WO | WO 2005/089673 A1 | 9/2005 |
| WO | WO 2008/079997 A2 | 7/2008 |
| WO | WO 2008/097498 | 8/2008 |

OTHER PUBLICATIONS

Vroman et al. Biodegradable Polymers. Materials (2009), v2, p. 307-344. (Year: 2009).*
Dolgin, "Encapsulating the problem, Cell therapy could cure type 1 diabetes—if only the immune system didn't get in the way," Nature, 540: s60-s62 (2016).
Fikes, Bradley J., "ViaCyte tries again with potential diabetes cure," The San Diego Union-Tribune, Oct. 18, 2017.
Pepper et al., "A Subcutaneous Cell Pouch™ as an Alternative to Intraportal Infusion of Islets of Langerhans to Restore Carbohydrate Control in the Diabetic Recipient," abstract only, 1 page.
Pepper et al., "Development of a novel, rapid and accurate pre-transplant in vitro assay to determine the in vivo function of the transplanted islets of langerhans," 2009 Joint Meeting of the International Pancreas and Islet Transplant Association (IPITA) and the International Xenotransplantation Association (IXA), Blackwell Publishing Ltd., abstract only (2009).
Sernova Corp. "Sernova and JDRF Announce Funding of Joint Research Collaboration to Advance Human Clinical Trials for the Treatment of Hypoglycemic Unawareness Patients with Severe Type 1 Diabetes" Press Release [online]. Retrieved from: http://www.sernova.com/press/?ID=205; on Jul. 12, 2016 (3 pages).
Sernova Corp. "Sernova Announces Interim Results from Key Preclinical Study With its Proprietary Cell Pouch System™" Press Release [online]. Retrieved from: http://www.sernova.com/press/?ID=114; on Mar. 16, 2010 (3 pages).
Sernova Corp. "Sernova Awarded Europe's Prestigious Horizon 2020 Grant to Fund Development of Cell-Based Hemophilia Therapeutic Product Into the Clinic" Press Release [online]. Retrieved from: http://www.sernova.com/press/?ID=193; on Dec. 21, 2015 (3 pages).
Sernova Corp. "Sernova Enters into Collaboration with Edmonton's Clinical Islet Transplant Program to Expand Cell Pouch™ Applications for Diabetes Treatment" Press Release [online]. Retrieved from: http://www.sernova.com/press/?ID=140; on Oct. 25, 2011 (3 pages).
Sernova Corp. "Sernova Corp Presents Key Data at International Transplant Conference" Press Release [online]. Retrieved from: http://www.sernova.com/press/?ID=134; on Jun. 6, 2011 (3 pages).
Sernova Corp. "Sernova Reports Positive Cell Pouch™ Performance in a Non-Human Primate Study" Press Release [online]. Retrieved from: http://www.sernova.com/press/?ID=131; on Feb. 28, 2011 (3 pages).
Sernova Corp. "Sernova-HemAcure Consortium Announce Significant Progress in Development of First in World Regenerative Medicine Therapy for Treatment of Hemophilia A Patients" Press Release [online]. Retrieved from: http://www.sernova.com/press/?ID=211; on Jul. 24, 2017 (3 pages).
Kriz et al., "Magnetic Resonance Imaging of Polypropylene Devices Implanted Subcutaneously or Into the Major Omentum As a Vehicle for Pancreatic Islet Transplantation: A Preliminary Investigation," abstract only (2009).
Kriz et al., "A Novel Technique to Surgically Implant a Polypropylene Scaffold Into the Omentum for the Transplantation of Pancreatic Islets," Joint Meeting of the International-Pancreas-and-Islet-Transplant-Association/International-Xenotransplantation-Association, Wiley-Blackwell Publishing, Inc, abstract only (2009).
Vilk et al., "Islet Transplantation in Pre-Vascularized Collagen Chambersplaced Subcutaneously or in the Omentum: A Comparative Study," abstract only.
Vilk et al., "The Age of Porcine Sertoli Cells Is Critical for Providing Immune Protection of Porcine Islets Xenografted Into Rats and Mice," abstract only.

(56) References Cited

OTHER PUBLICATIONS

Vilk et al., "Insulin Resistance and the Presence of Thymus-Independent Anti-Insulin IgG Antibody Production," abstract only.
White et al., "Long term survival and function of porcine islets co-transplanted with adult porcine islets co-transplanted with adult porcine sertoli cells into non-immunosuppressed rats and mice," Joint Meeting of the International-Pancreas-and-Islet-Transplant-Association/International-Xenotransplantation-Association, Wiley-Blackwell Publishing, Inc, abstract only (2009).
Bruni et al. "Islets Transplanted into a Prevascularized Subcutaneous Cell Pouch™ Demonstrates Long-Term Efficacy Measured by C-Peptide." Abstract submitted to the Canadian Society of Transplantation Annual Scientific Meeting, Mar. 2-5, 2011, Mont-Tremblant, Quebec. Final publication in Book of Abstracts, available online at: http://www.cst-transplant.ca/_Library/meetings_past_meetings/Book_of Abstracts_Feb16.pdf; Abstract No. 512, p. 23 (Feb. 16, 2011).
Mazzuca et al. "Islet Sparing Potential of a Subcutaneous Cell Pouch™ for Allogeneic Islet Transplantation." Abstract submitted to the 13th Congress of the International Pancreas and Islet Transplant Association (IPITA), Jun. 1-4, 2011, Prague, Czech Republic.
Moore et al. "Bioengineered stem cells as an alternative for islet cell transplantation." World J. Transplant., 5(1):1-10 (2015).
Motté et al. "Composition and function of macroencapsulated human embryonic stem cell-derived implants: comparison with clinical human islet cell grafts." Am. J. Physiol. Endocrinol. Metab., 307:E838-E846 (2014).
Pepper et al. "Development of a Cell Pouch to form an Artificial Pancreas." Abstract submitted to the American Society of Artificial Internal Organs 56th Annual Conference, May 27-29, 2010, Baltimore, Maryland. Final publication in ASAIO J., 56(2):134 (Mar./Apr. 2010).
Pepper et al. "Development of a rapid and accurate pre-transplant in vitro assay to determine the in vivo function of transplanted islets of Langerhans." Abstract submitted to the XXIII International Congress of the Transplantation Society, Aug. 15-19, 2010, British Colombia, Canada. Final publication in Transplantation, 90(2S):1010, Abstract 2440 (Jul. 27, 2010).
Pepper et al. "An Islet Sparing Transplant Technique Utilizing a Subcutaneous Cell Pouch™ as an Alternative to the Intraportal Route of Administration." Abstract submitted to the XXIII International Congress of the Transplantation Society, Aug. 15-19, 2010, British Colombia, Canada. Final publication in Transplantation, 90(2S):1010, Abstract 2531 (Jul. 27, 2010).
Pepper et al. "A Subcutaneous Cell Pouch™ as an Alternative to Intraportal Infusion of Islets of Langerhans to Restore Carbohydrate Control in the Diabetic Recipient." Abstract submitted to the Canadian Society of Transplantation Annual Scientific Meeting, Mar. 2-5, 2011, Mont-Tremblant, Quebec. Final publication in Book of Abstracts, available online at: http://www.cst-transplant.ca/_Library/meetings_past_meetings/Book_of Abstracts_Feb16.pdf; Abstract No. 510, pp. 22-23 (Feb. 16, 2011).

Pepper et al. "The Establishment of a Stringent Large Animal Model of Insulin-Dependent Diabetes." Abstract submitted to the Canadian Society of Transplantation Annual Scientific Meeting, Mar. 2-5, 2011, Mont-Tremblant, Quebec. Final publication in Book of Abstracts, available online at: http://www.cst-transplant.ca/_Library/meetings_past_meetings/Book_of Abstracts_Feb16.pdf; Abstract No. 514, p. 23 (Feb. 16, 2011).
Pepper et al. "A prevascularized subcutaneous device-less site for islet and cellular transplantation." Nat. Biotechnol., Advance Online Publication, doi:10.1038/nbt.3211; published Apr. 20, 2015 (8 pages).
Pepper et al. "Diabetes is Reversed in a Murine Model by Marginal Mass Syngeneic Islet Transplantation Using a Subcutaneous Cell Pouch Device." Transplantation, Online First e-publication, doi: 10.1097/TP.0000000000000864; accepted May 5, 2015. Final publication in vol. 99, pp. 2294-2300 (Nov. 2015).
De Vos et al., "Efficacy of a Prevascularized Expanded Polytetrafluoroethylene Solid Support System as a Transplantation Site for Pancreatic Islets" Transplantation, 63(6):824-830 (1997).
Desai et al., "Microfabricated immunoisolating biocapsules" Biotechnology and Bioengineering, 27(1):118-120 (1998) (abstract).
Griffith and Naughton, "Tissue Engineering—Current Challenges and Expanding Opportunities" Science, 295:1009-1014 (2002).
Howard et al., "Tissue engineering: strategies, stem cells and scaffolds" J. Anat., 213:66-72 (2008).
International Search Report and Written Opinion issued in International Patent Application No. PCT/US2010/047028, dated May 3, 2011.
Kulneva et al. "Mesenchymal Stem Cells for Bone Tissue Regeneration" Int. J. Med. Biol. Front., 17(9):981-997 (2011).
Morrison et al., "Culture in Reduced Levels of Oxygen Promotes Clonogenic Sympathoadrenal Differentiation by Isolated Neural Crest Stem Cells," J. Neurosci., 20(19):7370-7376 (2000).
Narang et al., "Biological and Biomaterial Approaches for Improved Islet Transplantation" Pharmacological Reviews, 58(2): 194-243 (2006).
Nilsson et al., "Can cells and biomaterials in therapeutic medicine be shielded off from innate immune recognition?" Trends Immunol., 31(1):32 (2010). doi:10.1016/j.it.2009.09.005. NIH Public Access Author Manuscript, available in PMC Jan. 1, 2011 (14 pages).
Smink et al., "Toward Engineering a Novel Transplantation Site for Human Pancreatic Islets" Diabetes, 62: 1357-1364 (May 2013).
Suzuki et al., "Function and Survival of Macroencapsulated Syngeneic Islets Transplanted Into Streptozocin-diabetic Mice" Transplantation, 66:21-28 (1998).
Vaithilingam et al., "Islet Transplantation and Encapsulation: An Update on Recent Developments" The Review of Diabetic Studies, 8(1): 51-67 (2011).
Wilson et al., "Challenges and emerging technologies in the immunoisolation of cells and tissues" Adv. Drug Deliv. Rev., 60(2): 124-145 (Jan. 14, 2008).
Singapore Patent Application No. 201201323-1, by Sernova Corp., filed Aug. 27, 2010: Written Opinion and Search Report, including Registrar's Letter, dated Jun. 25, 2013 (20 pages).

* cited by examiner

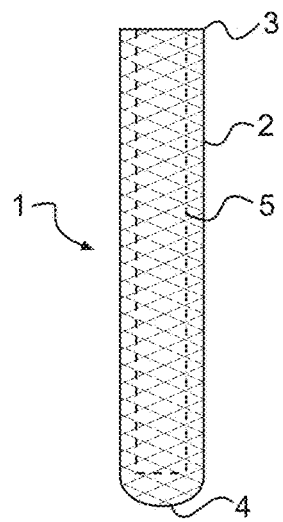
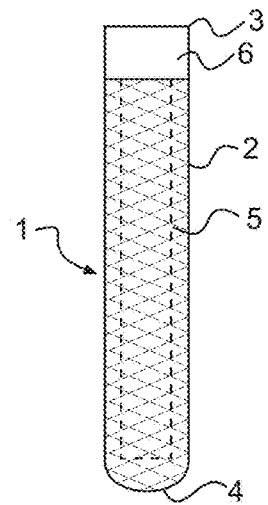
FIG. 1A  FIG. 1B
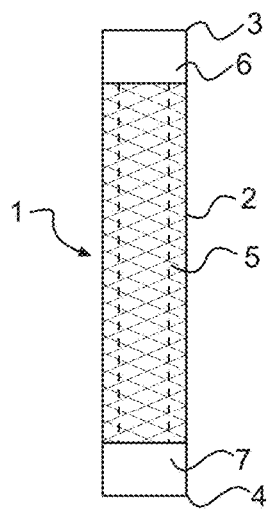
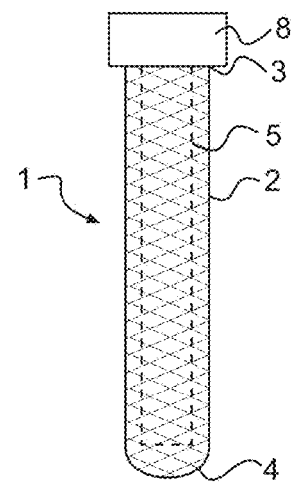
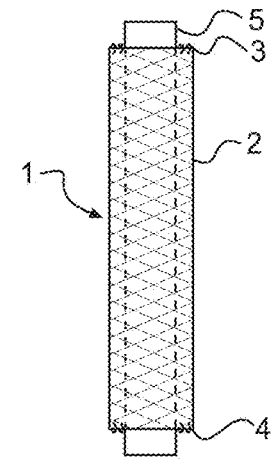
FIG. 1C  FIG. 1D  FIG. 1E

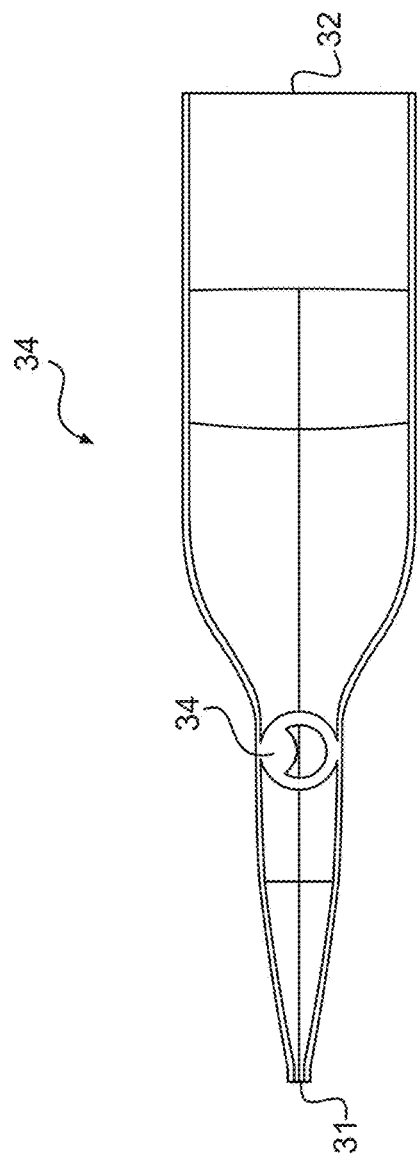
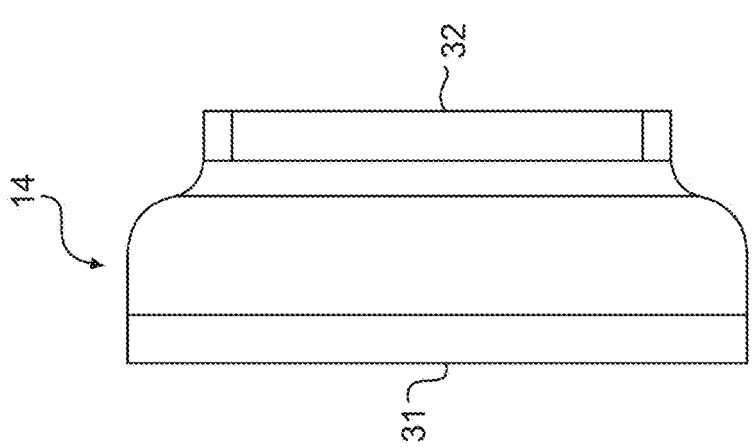
FIG. 5B
FIG. 5A

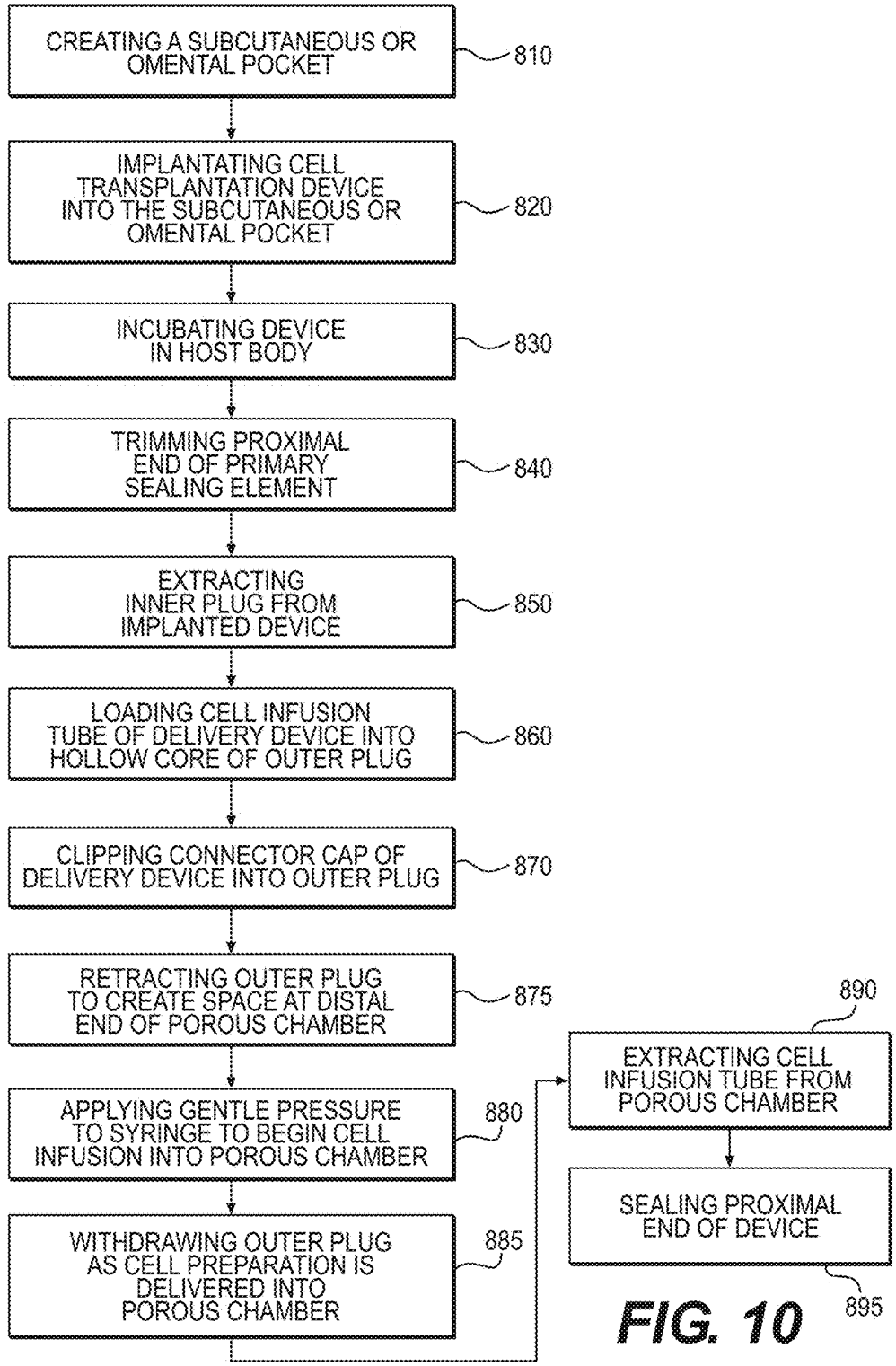

2 WEEKS (n=2)

| | MESH 1 | MESH 2 | MESH 3 | MESH 4 |
|---|---|---|---|---|
| AVERAGE COLLAGEN THICKNESS (mm) | 3.63 | 2.96 | 3.63 | 3.55 |
| BLOOD VESSELS PER $cm^2$ | 5.2 | 5.92 | 3.11 | 2.76 |

4 WEEKS (n=1)

| | MESH 1 | MESH 2 | MESH 3 | MESH 4 |
|---|---|---|---|---|
| AVERAGE COLLAGEN THICKNESS (mm) | 3.17 | 2.67 | 5.33 | 3.67 |
| BLOOD VESSELS PER $cm^2$ | 4.12 | 3.15 | 2.64 | 4.74 |

8 WEEKS (n=1)

| | MESH 1 | MESH 2 | MESH 3 | MESH 4 |
|---|---|---|---|---|
| AVERAGE COLLAGEN THICKNESS (mm) | 3.0 | 3.33 | 4.17 | 5.0 |
| BLOOD VESSELS PER $cm^2$ | 3.75 | 1.87 | 2.39 | 2.21 |

*FIG. 14*

METHODS AND DEVICES FOR CELLULAR TRANSPLANTATION

This application is a continuation of U.S. patent application Ser. No. 14/625,135, filed Feb. 18, 2015, which is a continuation of U.S. patent application Ser. No. 13/393,038 (now U.S. Pat. No. 9,011,899), which has a § 371(c) date of Jun. 13, 2012 and is a national phase entry of PCT/US2010/047028, filed Aug. 27, 2010, and which claims priority to U.S. Provisional Application No. 61/238,011, filed Aug. 28, 2009, all of which are incorporated herein by reference in their entirety.

The present disclosure is related to the field of cellular therapy, and more specifically, to methods and devices for transplantation of cells into a host body.

Recent discoveries in the field of cellular therapy present new opportunities for the use of cell transplantation in disease areas with critical, unmet medical needs. Currently, there are no fully effective drug therapies for many acquired and congenital disease conditions, such as diabetes or Parkinson's disease, which are caused by loss of or damage to cells producing biomolecules necessary for control of physiological functions. Cellular therapy holds the promise of replacing lost or damaged cells with donor cells or stem cells to improve the impaired physiological functions. For example, transplantation of islets of Langerhans cells would provide a means of restoring carbohydrate control in patients with insulin-dependent diabetes. Similarly, transplantation of dopaminergic neurons or neural stem cells has emerged as a promising cell-based therapy for Parkinson's disease.

Major limiting factors in the application of cellular therapy is the difficulty in transplanting cells into host tissue and ensuring that the transplanted cells continue to function without eliciting an immune response or causing other harmful side effects in the host. Attempts have been made to administer therapeutic cells directly into the host body, e.g., in the vascular system or by implantation in an organ or tissue. However, with direct cellular transplantation, the patient is required to remain on life-long immunosuppressant therapy, and the immunosuppressant drugs can cause toxicity to the host and the implanted cells. Additionally, direct exposure of the cells to blood may lead to an immediate blood-mediated inflammatory reaction (IBMIR) that initiates a coagulation cascade and can destroy a significant portion of the transplanted cells. Furthermore, cells may become lodged in microvessels and cause blockage and thrombosis of the vessels, which may result in a loss of function of the transplanted cells and damage to local tissue.

Another therapeutic approach is the delivery of cells using devices that provide a biologically suitable environment for the cells to reside in the host body. Major challenges with this approach are poor incorporation of blood vessels into the device for nourishing the cells and maintaining an optimal environment within the device for long-term survival of the cells. In the absence of an immediately vascularized environment, transplanted cells are not able to obtain enough oxygen or easily eliminate wastes, and may rapidly die or become damaged through the effects of ischemia or hypoxia. Furthermore, even in situations where some vessels grow early on, the vessels may not be sustained. In addition, the natural inflammatory cascade of the body may also result in the death of or damage to cells. Some of the other difficulties encountered with this approach include excessive scarring and/or walling off of the device, incompatibility of the device material with the biological milieu, difficulties in imaging the device and the implantation environment, improper dimensions of the device affecting biological function of the cells, inability to load the appropriate number of cells for a sustained therapeutic effect, and difficulty in removing the device when it needs replacement. Furthermore, the device configuration may not be amenable to the external contours of the body, which can result in abnormal protrusions of the device making the device unacceptable to the patient from an aesthetic perspective.

Thus, there still remains a need to find an effective technique for successful transplantation of therapeutic cells. The present disclosure provides methods and devices for delivering and maintaining cells in vivo for an extended period of time, while alleviating many of the problems associated with existing device-based cell therapy approaches.

In one aspect of the present disclosure, a device for transplanting cells in a host body is provided. The device comprises a porous scaffold comprising at least one chamber having a proximal end and a distal end, and at least one removable plug configured to be positioned within the at least one chamber. The porous scaffold comprises a mesh having pores sized to facilitate growth of vascular and connective tissues into the at least one chamber. In some embodiments, the porous scaffold comprises a polypropylene mesh.

Another embodiment of the present disclosure is a device for implanting cells in a host body, wherein the device comprises a porous scaffold comprising one or more chambers having a proximal end and a distal end, and an opening at either or both the proximal end and the distal end. The porous scaffold comprises pores sized to facilitate growth of vascular and connective tissues into the one or more chambers. The device also comprises one or more two-plug systems comprising an outer plug configured to be positioned within the one or more chambers, and an inner plug configured to be positioned within the outer plug. Additionally, the device comprises at least one seal configured to enclose the plug system in the chamber and enclose the opening at either or both the proximal end and the distal end of the chamber.

In another aspect of the present disclosure, a method of transplanting cells in a host body is provided. The method comprises the steps of implanting a device for holding cells in the host body, wherein the device comprises a porous scaffold comprising at least one chamber having a proximal end and a distal end. The porous scaffold comprises a mesh having pores sized to facilitate growth of vascular and connective tissues into the at least one chamber. In some embodiments, the porous scaffold comprises a polypropylene mesh. The device further comprises at least one plug configured to be positioned within the at least one chamber, and the least one chamber comprises an opening at either or both the proximal end and the distal end. The method comprises the steps of closing the opening at either or both the proximal end and the distal end of the chamber after implanting the device. The method further comprises maintaining the device in the host body until the porous scaffold is infiltrated with vascular and connective tissues, accessing the device through a surgical incision, reopening either or both the proximal end and the distal end of the chamber, extracting the plug from the chamber to create a space within the porous scaffold that is encapsulated in vascularized collagen matrix, delivering a cell preparation into the vascularized space, and reclosing the opening at either or both the proximal end and the distal end of the chamber.

In another alternate embodiment, the method of implanting cells in a host body provides an implantable device for holding cells in the host body, wherein the implantable device comprises a porous scaffold having pores sized to facilitate growth of vascular and connective tissues into the porous scaffold, at least one two-plug system configured to be positioned within the porous scaffold. The porous scaffold of the implantable device comprises at least one chamber having an opening at either or both a proximal end and a distal end of the chamber. The device comprises a seal to enclose the opening at either or both the proximal and distal ends of the at least one chamber. The at least one plug system of the implantable device comprises an outer plug configured to be positioned within the at least one chamber and an inner plug configured to be positioned within the outer plug. The method further comprises the steps of implanting the device in the host body, maintaining the device in the host body until the device is infiltrated with vascular and connective tissues, and providing a cell delivery device comprising at least one cell infusion tube loaded with a cell preparation, wherein the cell infusion tube is configured to be positioned within the outer plug of the at least one plug system. Additionally, the method comprises accessing the implanted device through a surgical incision and opening the seal at either or both the proximal end and the distal end of the device, withdrawing the inner plug from the plug system, inserting the cell infusion tube into the outer plug, withdrawing the outer plug from the at least one chamber and simultaneously infusing the chamber with the cell preparation, and reclosing the seal. It is to be understood that both the foregoing general description and the following detailed description are exemplary and explanatory only and are not restrictive of the invention, as claimed.

Another aspect of the disclosure provides a cellular transplantation device comprising a porous scaffold having pores sized to facilitate growth of vascular and connective tissues into the porous scaffold comprising at least one chamber and preferably between 2-12 chambers, wherein the porous scaffold is coated with a biocompatible, biodegradable material designed to temporarily fill the pores of the scaffold. In certain embodiments, the porous scaffold comprises a polypropylene mesh. Suitable biocompatible, biodegradable materials include, e.g., collagen, fibronectin, extracellular matrix proteins, and membrane cytoskeletal proteins. The disclosure also provides a method for transplanting cells into a host body comprising implanting a transplantation device comprising a porous scaffold having pores sized to facilitate growth of vascular and connective tissues into the porous scaffold comprising at least one chamber and preferably between 2-12 chambers, wherein the porous scaffold is coated with a biocompatible, biodegradable material that temporarily fills the pores of the scaffold, and wherein the at least one chamber is filled with the cells to be transplanted and the chamber is sealed.

The accompanying drawings, which are incorporated in and constitute a part of this specification, together with the description, illustrate methods and embodiments of the invention.

BRIEF DESCRIPTION OF DRAWINGS

FIGS. 1A-1E illustrate various embodiments of a single-chamber cell transplantation device consistent with the present disclosure;

FIG. 5A illustrates a seal of a cell transplantation device consistent with an embodiment of the present disclosure;

FIG. 5B is a cross-sectional view of the seal shown in FIG. 5A;

FIG. 10 is a flow chart showing the steps of a cell transplantation method in accordance with the present disclosure;

FIG. 14 is table of the average collagen thickness and total blood vessel/cm$^2$ calculated for four cell transplantation devices consistent with embodiments of the present disclosure, as described in Example 3;

DESCRIPTION OF EXEMPLARY EMBODIMENTS

Figure 1F:
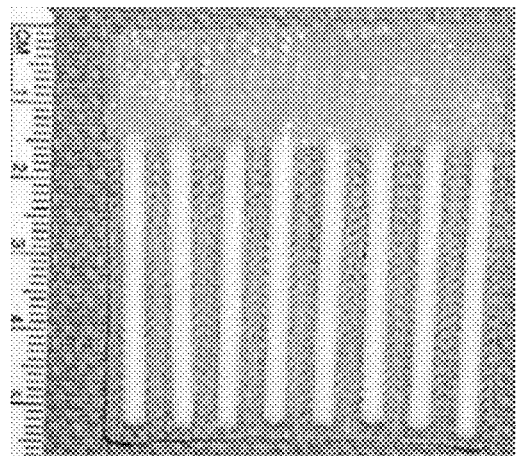
FIG. 1F illustrates an embodiment of a multi-chamber cell transplantation device consistent with the present disclosure.

Reference will now be made in detail to embodiments of this disclosure, examples of which are illustrated in the accompanying drawings. Wherever possible, the same reference numbers will be used throughout the drawings to refer to the same or like parts. Throughout the disclosure, the terms cell infusion and cell transplantation are used interchangeably.

A cell transplantation device for containing therapeutic cells in vivo is provided. In one exemplary embodiment, the cell transplantation device comprises at least one porous scaffold comprising a chamber therein and having an opening at either or both a proximal end and a distal end of the scaffold, and at least one plug configured to be housed in the chamber. The opening at one or both the ends of the chamber are sized to enable insertion and retraction of the plug from the chamber. In one embodiment, the at least one porous scaffold is tubular in shape, and the at least one plug is cylindrical and extends along a lumen of the at least one porous scaffold. In some embodiments, the porous scaffold is open only at the proximal end. In one such embodiment, the distal end of the tubular porous scaffold comprises a rounded or flat-bottomed surface. In another embodiment, the edges at the distal end of the porous scaffold are tapered and brought into contact with one another to seal the distal end.

In another exemplary embodiment, the cell transplantation device comprises a porous scaffold comprising one or more chambers having a proximal end and a distal end. The one or more chambers comprise an opening at the proximal end. The device also comprises one or more plug systems comprising an outer plug configured to be positioned within the one or more chambers, and an inner plug configured to be positioned within the outer plug. Additionally, the device comprises at least one seal configured to enclose the plug system within the chamber and seal the opening at the proximal end of the chamber.

The porous scaffold is formed of a biocompatible material that should elicit only a mild inflammatory response in the body. The mild inflammatory components stimulate angiogenesis and promote incorporation of a vascularized collagen matrix into the device, but do not result in significant inflammation around the device. An example of such a biocompatible material is polypropylene. In exemplary embodiments, the porous scaffold comprises a woven polypropylene mesh that has sufficient stiffness to facilitate device fabrication. The polypropylene mesh is also selected to allow microvessels to enter the device and be maintained as robust, healthy vessels, which is critical for the survival and normal functioning of the therapeutic cells infused into the device.

By encouraging regulated growth of vascularized tissue into the device, the porous scaffold prevents encapsulation of the device with scar tissue. Ingrown tissues also stabilize the implant and prevent inadvertent movement of the device in situ. Additionally, in some embodiments, the porous scaffold is coated with biological or non-biological agents to stimulate tissue incorporation and angiogenesis, for example, growth factors. The device may be dip-coated in a polymer-drug formulation or other known technique to apply the coating to the device. Examples of biological or non-biological agents to stimulate tissue incorporation and angiogenesis include but are not limited to: VEGF (vascular endothelial growth factor), PDGF (platelet-derived growth factor), FGF-1 (fibroblast growth factor), NRP-1 (neuropilin-1), Ang-1, Ang2 (angiopoietin 1,2), TGF-ß, endoglin, MCP-1, αvß3, αvß5, CD-31, VE-cadherin, ephrin, plasminogen activators, angiogenin, Del-1, aFGF (acid fibroblast growth factor), vFGF (basic fibroblast growth factor), follistatin, G-CSF (granulocyte colony-stimulating factor), HGF (hepatocyte growth factor), Il-8 (interleukin-8), Leptin, midkine, placental growth factor, PD-ECGF (platelet-derived endothelial growth factor), PTN (pleiotrophin), progranulin, proliferin, TGF-α, and TNF-α.

In some embodiments, the outer surface of the porous scaffold is roughened to stimulate tissue ingress. In certain embodiments, the porous scaffold includes various drug-eluting polymer coatings. In other embodiments, the porous scaffold may be coated with a biodegradable or non-biodegradable polymer without a drug. The scaffold may be partially or completely coated with the polymer. Representative polymers that can be used for coating and/or drug elution include but are not limited to: methacrylate polymers, polyethylene-imine and dextran sulfate, poly(vinylsiloxane)ecopolymerepolyethyleneimine, phosphorylcholine, poly(ethyl methacrylate), polyurethane, poly(ethylene glycol), poly(lactic-glycolic acid), hydroxyapetite, poly(lactic acid), polyhydroxyvalerte and copolymers, polyhydroxybutyrate and copolymers, polycaprolactone, polydiaxanone, polyanhydrides, polycyanocrylates, poly(amino acids), poly(orthoesters), polyesters, collagen, gelatin, cellulose polymers, chitosans, and alginates or combinations thereof. Additional examples that may be used to coat the scaffold include but are not limited to: collagen, fibronectin, extracellular matrix proteins, vinculin, agar, and agarose. It should be understood that various mixture of the polymers may be used.

With respect to drug elution, in some illustrative embodiments, the porous scaffold includes an antibiotic coating to minimize infections. Representative antibiotics include but are not limited to: ampicillin, tetracycline, nafcillin, oxacillin, cloxacillin, dicloxacillin, flucloxacillin, vancomycin, kanamycin, gentamicin, streptomycin, clindamycin, trimethoprim-sulfamethoxazole, linezolid, teicoplanin, erythromycin, ciprofloxacin, rifampin, penicillin, amoxicillin, sulfonamides, nalidixic acid, norfloxacin, ciprofloxacin, ofloxacin, sparfloxacin, lomefloxacin, fleroxacin, pefloxacin, amifloxacin, 5-fluorouracil, chloramphenicol, polymyxin, mitomycin, chloroquin, novobiocin, nitroimadazole. In another embodiment the porous scaffold includes a bactericidal agent. Representative bactericidal agents include but are not limited to: benzalkonium chloride, chlorohexidine gluconate, sorbic acid and salt thereof, thimerosal, chlorobutanol, phenethyl alcohol, and p-hydroxybenzoate.

In some other embodiments, parts of the cell transplantation device are coated with antifibrotic drugs to inhibit fibrous tissue encapsulation. Representative antifibrotic agents include but are not limited to: paclitaxel, everolimus, tacrolimus, rapamycin, halofuginone hydrobromide, combretastatin and analogues and derivatives thereof (such as combretastatin A-1, A-2, A-3, A-4, A-5, A-6, B-1, B-2, B-3, B-4, D-1, D-2, and combretastatin A-4 phosphate (Oxigene)), docetaxel, vinblastine, vincristine, vincristine sulfate, vindesine, and vinorelbine, camptothecin topotecan, irinotecan, etoposide or teniposide anthramycin, mitoxantrone, menogaril, nogalamycin, aclacinomycin A, olivomycin A, chromomycin $A_3$, and plicamycin, methotrexate, edatrexate, trimetrexate, raltitrexed, piritrexim, denopterin, tomudex, pteropterin, and derivatives and analogues thereof. In some embodiments, the cell transplantation device may also include polymethyl methacrylate or bone cement or other types of cyanoacrylates.

In some embodiments, the porous scaffold is formed of a material that allows imaging of the implanted device using, for example, MRIs, fMRIs, CT scans, X-rays, ultrasounds, PET scans, etc. In one such embodiment, the porous scaffold comprises a polymer mesh (for example, polypropylene, polytetrafluoroethylene (PTFE), polyurethane, polyesters, silk meshes, etc.) that is immunologically compatible and allows imaging of the neovascularized tissue. In another embodiment, the porous scaffold comprises a combination of materials. In one such embodiment, the porous scaffold comprises interwoven polypropylene and silk strands.

The pore size of the scaffold material is selected to facilitate tissue incorporation and vascularization within the chamber of the porous scaffold. In some embodiments, the pore sizes may range from about 50 nm to 5 mm. In one exemplary embodiment, the porous scaffold comprises a woven polypropylene mesh with 0.53 mm pore diameter.

In some embodiments, the pore size is selected to exclude immune cells or immune agents from penetrating the implanted device. In some other embodiments, the pore size does not necessarily need to exclude immune cells or immune agents from infiltrating the device. This would be the case, for example, when the device is used to transplant a combination of cells, including immunoprotective cells, (e.g. Sertoli cells, mesenchymal stem cells, etc.) which can provide immune protection to the co-transplanted cells. This would also be the case, for example, when the device is used to transplant syngeneic cells, or cells derived from the patient receiving the transplant.

The plug or plug system of the cell transplantation device is configured to fit into the chamber within the porous scaffold. The plug or plug system may comprise a nonporous material (e.g., polytetrafluoroethylene (PTFE), polypropylene, etc.) that inhibits ingrowth of biological tissue into the plug or plug system. The plug or plug system may be a hollow or solid structure. However, if a hollow plug is used, care should be taken to prevent infiltration of collagen or any other biological material into the lumen of the plug when the device is implanted into host tissue. The plug system is discussed in further detail below.

In some embodiments, the proximal end of the plug or plug system is connected to a seal. In such embodiment, the seal is configured to close the proximal opening of the chamber when the plug or plug system is completely inserted into the chamber of the porous scaffold. The seal is structured to hold the plug or plug system in place inside the porous scaffold. In another embodiment, the seal is separate from the plug or plug system. In yet another embodiment, the seal is connected to the porous scaffold. Further, in some exemplary embodiments, the proximal end of the chamber is closed using surgical sutures and/or vascular clips without using a separate seal.

When implanted in a host body, the porous scaffold of the device encourages ingrowth of vascular and connective tissue, such that the plug or plug system housed within the scaffold becomes encapsulated in a vascularized tissue matrix. When the plug or plug system is removed from the porous scaffold, a neovascularized chamber is created within the device, which can then be used for holding a cell preparation in the host body.

The sizes of the porous scaffold and the plug or plug system are selected to provide an optimal surface area-to-volume ratio for holding cells in vivo and for ensuring long-term survival of the cells within the neovascularized chamber. Similarly, the number of chambers in the transplantation device is determined based on the volume and/or number of cells that are to be transplanted. In some embodiments, the total volume of the cell transplantation device is adjusted by increasing or decreasing the number of chambers while maintaining an optimum surface area-to-volume ratio of each individual chamber. In other embodiments the length of the chambers is adjusted to alter the total volume. Alternatively, in various embodiments, the cell transplantation device comprises a fixed number of chambers, but only a selected number of chambers are infused with cells depending on the total volume requirement of the device. In other embodiments the length of the chambers is adjusted as well as the number of chambers to alter the total volume required.

The cell transplantation device disclosed can be implanted either subcutaneously or intraperitoneally in a host body, including the omentum or other appropriate site. Alternatively, the cell implantation device disclosed can be implanted partially intraperitoneally in a host body, including into the omentum or other appropriate site and extend into the subcutaneous environment. In one embodiment the cells may be loaded in the portion of the device extending into the subcutaneous environment while the rest of the device is in the intraperitoneal environment. In another embodiment the cell transplantation device may be implanted into the brain, spinal cord area or any other organ as required to elicit a therapeutic effect from transplanted cells. In most instances, the host is a human, but may be another mammal or non-mammalian animal. The cell transplantation procedure is a two-step process comprising a device implantation step followed by a cell infusion (cell transplantation) step. The cell infusion step is implemented after an in vivo incubation period during which the implanted device is infiltrated with a vascularized collagen matrix. In one embodiment, the incubation period is approximately thirty days, which allows adequate time for angiogenesis and collagen infiltration of the porous scaffold. The incubation period may be lengthened or shortened, depending on the degree of neovascularization and tissue (collagen with cells) formation needed or desired. For example, transplantation devices may vascularize at different rates depending on the device material, dimensions, or coatings, such as, for example, antibiotic coatings, growth factors, etc. Transplantation devices may also vascularize at different rates in different hosts, or when located in different body tissues within the same host. It is within the skill of a person in the art to determine the appropriate incubation period. For example, imaging studies may be performed prior to delivering cells to ensure that adequate vascular and/or connective tissue is deposited around and through the walls of the porous scaffold during the incubation period. For the cell infusion step, the implantation site is accessed through a surgical incision, and the plug or plug system is removed from the porous scaffold to create a collagen and blood vessel lined pocket within the scaffold. The cell preparation is then delivered into the vascularized pocket, and the porous scaffold is re-sealed. In another embodiment the cell transplantation procedure is a single step process whereby the device is placed and the cells implanted at the same time. In this circumstance, the cells may be placed in a matrix so that they do not leak through the pores of the device or alternatively the device may be coated with a degradable polymer to prevent cells from leaking from the device during the process of collagen and angiogenesis development.

In some embodiments, the cells to be transplanted may be combined with a biocompatible viscous solution or biodegradable polymer formulation prior to being loaded into the chamber of any of the transplantation devices described herein. This biodegradable polymer will protect the cells until the device is fully vascularized by the host body. These formulations may be placed in the chambers prior to or following placement of the device in a host, but before a collagen matrix and vascular structures have formed in the device. Cells combined with a biocompatible viscous solution or biodegradable polymer formulation will be particularly useful in devices designed to be loaded with cells prior to implantation of the device in the host body. Representative polymers that can be used as a biodegradable formulation in conjunction with cells include but are not limited to: polyethylene-imine and dextran sulfate, poly(vinylsiloxane) ecopolymerepolyethyleneimine, phosphorylcholine, poly(ethylene glycol), poly(lactic-glycolic acid), poly(lactic acid), polyhydroxyvalerte and copolymers, polyhydroxybutyrate and copolymers, polydiaxanone, polyanhydrides, poly(amino acids), poly(orthoesters), polyesters, collagen, gelatin, cellulose polymers, chitosans, alginates, fibronectin, extracellular matrix proteins, vinculin, agar, agarose, hyaluronic acid, matrigel and combinations thereof.

It should be noted that cells may be placed in the device; however, the cells may also be encapsulated. The following are by way of example and not by way of limitation. Examples of polymeric cell encapsulation systems include alginate encapsulating, polysaccharide hydrogels, chitosan, calcium or barium alginate, a layered matrix of altinate and polylysine, photopolymerizable poly(ethylene glycol) polymer to encapsulate individual cells or cell clusters, polyacrylates including hydroxyethyl methacrylate methyl methacrylate, silicon capsules, silicon nanocapsules, and polymembrane (acrylonitrile-co-vinyl chloride).

FIGS. 1A-1E illustrate various exemplary embodiments of a cell transplantation device 1. Device 1 comprises a polymer mesh (e.g. a polypropylene mesh, a PTFE mesh, or any other suitable material) that forms a porous chamber 2 for containing cells in a host body. In some embodiments, device 1 may comprise 1, 2, 3, 4, 5, 6, 7, 8, 9, 10, 11, 12 or more porous chambers 2. The availability of multiple chambers allows the use of any number or combination of chambers depending on the volume of cellular preparation required, which is within the knowledge and skill of persons skilled in the art to determine.

As shown in FIG. 1A, device 1 comprises a proximal end 3, a distal end 4, and a plug 5 housed in porous chamber 2. In one embodiment, porous chamber 2 is tubular in shape, and plug 5 is cylindrical and extends along a lumen of porous chamber 2. In another exemplary embodiment, porous chamber 2 comprises an opening at proximal end 3. The opening at proximal end 3 is sized to enable insertion and retraction of plug 5 from porous chamber 2. In one such embodiment, the opening at proximal end 3 is sealed using surgical sutures and/or vascular clamps during device incubation and after infusion of cells into the device. As would be understood by a person of ordinary skill in the art, any other surgical sealing element, for example, microvascular clips, clamps, etc., can be used to seal the opening at proximal end 3. In another embodiment, device 1 comprises a non-porous flap 6 at proximal end 3, as illustrated in FIG. 1B. In one such embodiment, flap 6 is made of silicone. Flap 6 can be sealed using surgical sutures, clamps or any other suitable sealing mechanism during device incubation and after infusion of cells into the device. In an exemplary embodiment, distal end 4 of device 1 comprises a rounded or flat-bottomed surface. In another embodiment, device 1 comprises an opening at distal end 4, which can be sealed using surgical sutures, clamps or any other surgical sealing element, during device incubation and after infusion of cells. In yet another exemplary embodiment, as shown in FIG. 10, distal end 4 comprises a non-porous portion 7, which prevents tissue ingrowth at the distal end of the device and facilitates retraction of plug 5 from the device prior to cell infusion.

In some embodiments, as illustrated in FIG. 1D, the proximal end of plug 5 is connected to a seal 8. In such an embodiment, seal 8 is configured to close the opening at proximal end 3 when plug 5 is inserted into chamber 5. Seal 8 is structured to hold plug 5 in place inside the porous chamber. In another embodiment, plug 5 is longer than porous chamber 2 and acts as a seal on both proximal end 3 and distal end 4 of the device, as shown in FIG. 1E. The edges of porous chamber 2 around plug 5 are sealed using surgical sutures and/or surgical glue. After removal of plug 5 prior to cell infusion, the openings at proximal end 3 and distal end 4 can be sealed using surgical sutures, vascular clamps, or any other suitable sealing mechanism, as would be understood by one of ordinary skill in the art.

In some exemplary embodiments, device 1 comprises multiple porous chambers 2 that are laterally connected to each other. In one such embodiment, the multiple porous chambers 2 are formed, for example, by ultrasonically welding the top and bottom surfaces of a porous material along a line substantially parallel to a longitudinal axis of the device. FIG. 1F illustrates a cell transplantation device having eight porous chambers 2. Each chamber 2 houses a plug 5 during the device incubation phase. Plugs 5 are removed from chambers 2 prior to infusion of cells into the chambers. In one embodiment, device 1 comprises eight porous chambers and has an overall length of 50 mm and width of 45 mm. Each porous chamber 2 has an inner diameter no greater than 3.5 mm and houses a plug 5 having a length of approximately 40 mm and diameter 2.5 mm. In such an embodiment, plug 5 is formed of a non-porous, biocompatible material, for example, polytetrafluoroethylene (PTFE).

Figure 2A:
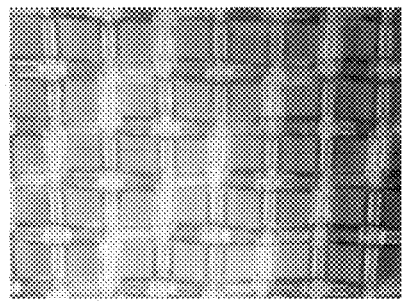
FIGS. 2A-2D illustrate various mesh configurations that may be used for forming a cell transplantation device consistent with the present disclosure.
Figure 2B:
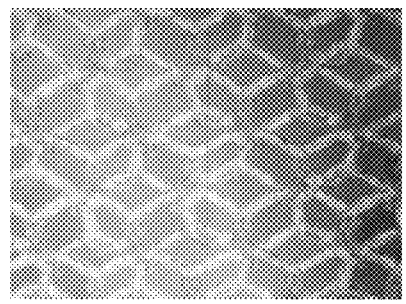
Figure 2C:
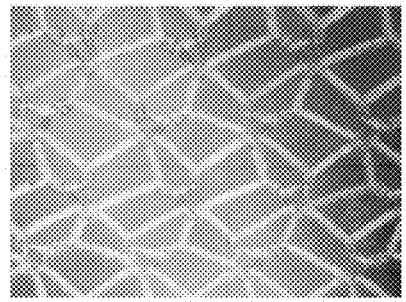
Figure 2D:
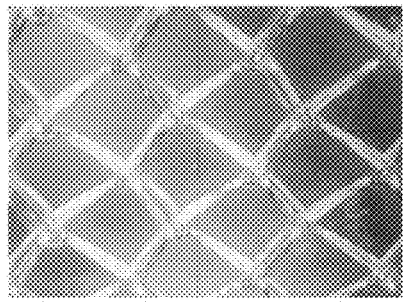

Exemplary embodiments of the cell transplantation device of the present disclosure are formed of medical grade polypropylene meshes, for example, Polypropylene Knitted Mesh (PPKM) purchased from SURGICALMESH™, Brookfield, Conn., USA. In illustrative embodiments, the meshes are formed of monofilaments ranging in diameter from 0.1 mm to 0.3 mm, and mesh pore sizes ranging from 0.3 mm to 1 mm, from 0.4 mm to 0.85 mm and 0.5 mm to 0.6 mm. FIGS. 2A-2D illustrate various exemplary mesh configurations that can be used for forming the cell transplantation devices. FIG. 2A illustrates a polypropylene mesh (PPKM601) having a pore size of 0.5 mm and monofilament thickness of 0.3 mm; FIG. 2B shows a polypropylene mesh (PPKM602) having a pore size of 0.53 mm and monofilament thickness of 0.18 mm; FIG. 2C shows a polypropylene mesh (PPKM404) having a pore size of 0.53 mm and monofilament thickness of 0.13 mm; and FIG. 2D shows a polypropylene mesh (PPKM604) having a pore size of 0.85 mm and monofilament thickness of 0.2 mm.

Figure 3A:
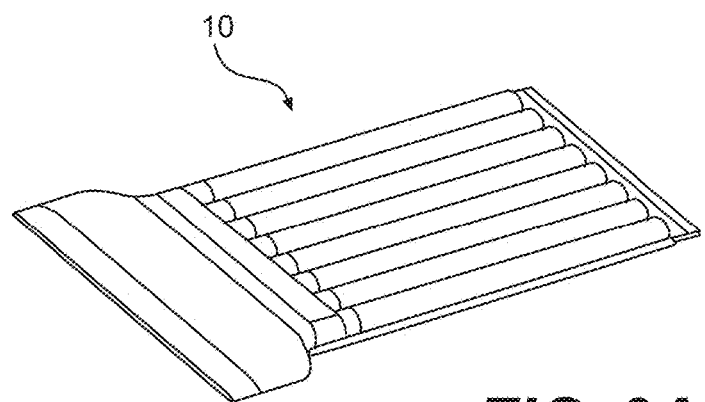
FIG. 3A illustrates a cell transplantation device in accordance with an embodiment of the present disclosure.
Figure 3B:
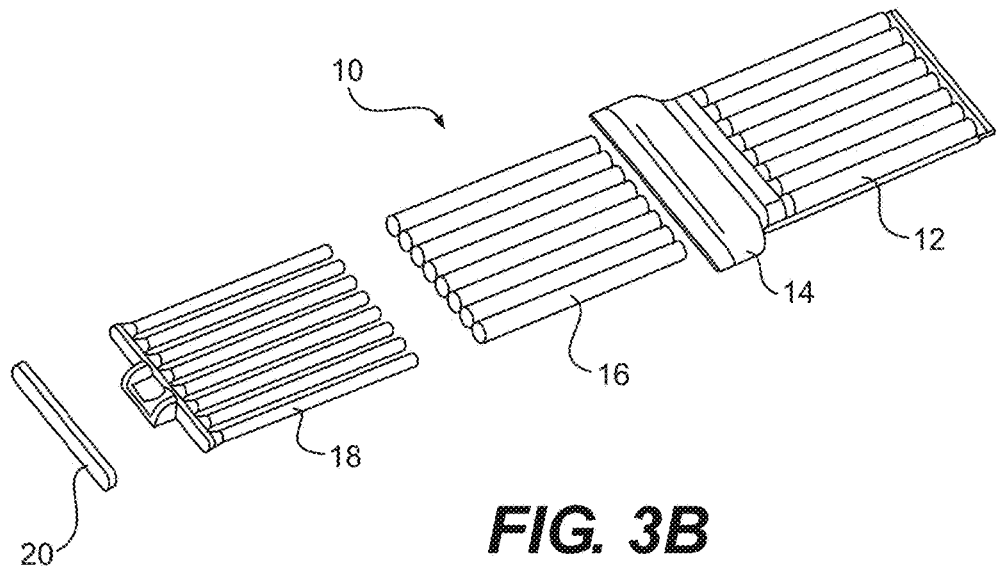
FIG. 3B illustrates the components of the cell transplantation device of FIG. 3A.

FIG. 3A illustrates another exemplary embodiment of a cell transplantation device 10. FIG. 3B illustrates the components of the cell transplantation device 10. Device 10 comprises a porous scaffold 12, a primary seal 14, at least one plug system comprising an outer plug 16 and an inner plug 18, and a secondary seal 20.

Figure 4:
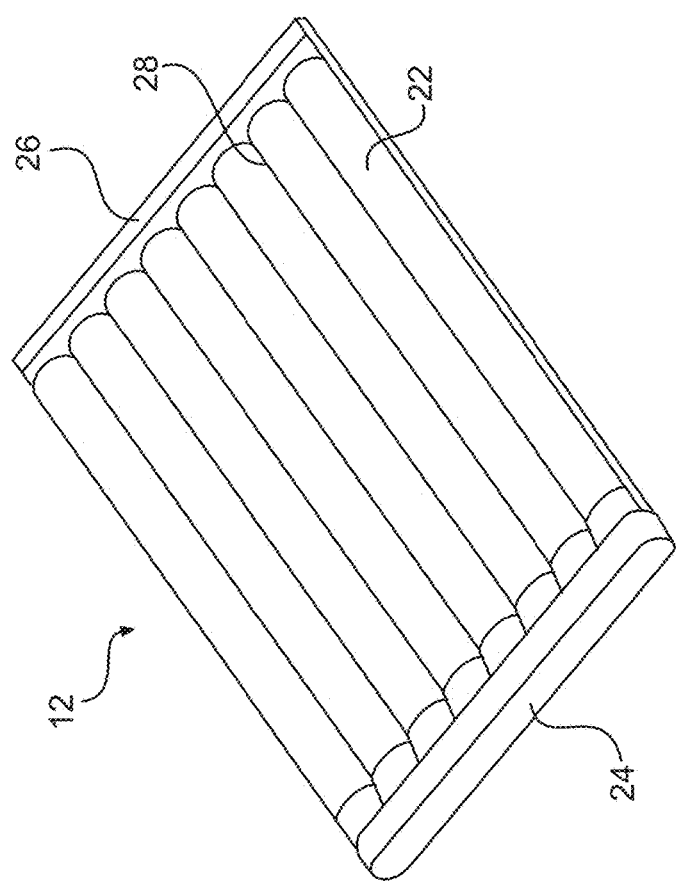
FIG. 4 illustrates a porous scaffold of a cell transplantation device consistent with an embodiment of the present disclosure.

As illustrated in FIG. 4, porous scaffold 12 of cell transplantation device 10 may comprise a polymer mesh (e.g. a polypropylene mesh, a PTFE mesh, or any other suitable material) that forms one or more porous chambers 22 for containing cells in a host body. In some embodiments, the porous scaffold 12 may comprise 1, 2, 3, 4, 5, 6, 7, 8, 9, 10, 11, 12 or more porous chambers 22. The availability of multiple chambers allows the use of any number or combination of chambers depending on the volume of cellular preparation required, which is within the knowledge and skill of persons skilled in the art to determine.

Porous chambers 22 may be created, for example, by joining the top and bottom surfaces of porous scaffold 12 along a line substantially parallel to a longitudinal axis of the device. Multiple porous chambers 22 may have equal or different cross-sectional dimensions and surface areas. In one embodiment, multiple porous chambers 22 are formed by ultrasonically welding the polymer mesh from a proximal end 24 to a distal end 26 of the scaffold. The top and bottom surfaces of porous scaffold 12 are continuous across the one or more porous chambers 22, interrupted only by ultrasonic weld lines 28, which run substantially parallel to a longitudinal axis of porous scaffold 12. The top and bottom surfaces of porous scaffold 12 can be indented slightly at each weld line, which offers additional surface area for vascularization and provides physical stability to device 10 within a host. In one embodiment, the edges at distal end 26 are tapered and ultrasonically welded to one another to seal the distal end 26.

With reference to FIG. 3B, primary seal 14 is configured to seal the one or more porous chambers 22 during device incubation and after cell infusion. Primary seal 14 comprises an inert and biocompatible polymeric film or any other suitable material. In one embodiment, primary seal 14 is ultrasonically welded at the lateral edges and at the tapered proximal end 31, as illustrated in FIGS. 5A and 5B. Distal end 32 of primary seal 14 is attached to proximal end 24 of porous scaffold 12. In one embodiment, distal end 32 is ultrasonically welded to proximal end 24 of porous scaffold 12.

In various embodiments, primary seal 14 comprises a re-sealable lock 34, which assists in maintaining the at least one outer plug 16 within a porous chamber 22 during the incubation period. Lock 34 also prevents leakage of cellular preparation during the cell infusion process. Any suitable re-sealable locking mechanism may be used as lock 34. In one embodiment, lock 34 comprises interlocking groove and ridge features, which form a tight seal when pressed together and unlocks when the top and bottom surfaces of seal 14 are pulled apart at the proximal end 31. Following the device incubation period, access to outer plug 16 is achieved by trimming proximal end 31 of primary seal 14 and opening re-sealable lock 34. After the cell preparation is delivered into porous scaffold 12, lock 34 is reclosed and proximal end 31 is re-sealed using, e.g., surgical sutures, staples or bio-adhesives, or hermetic seals.

Figure 6A:
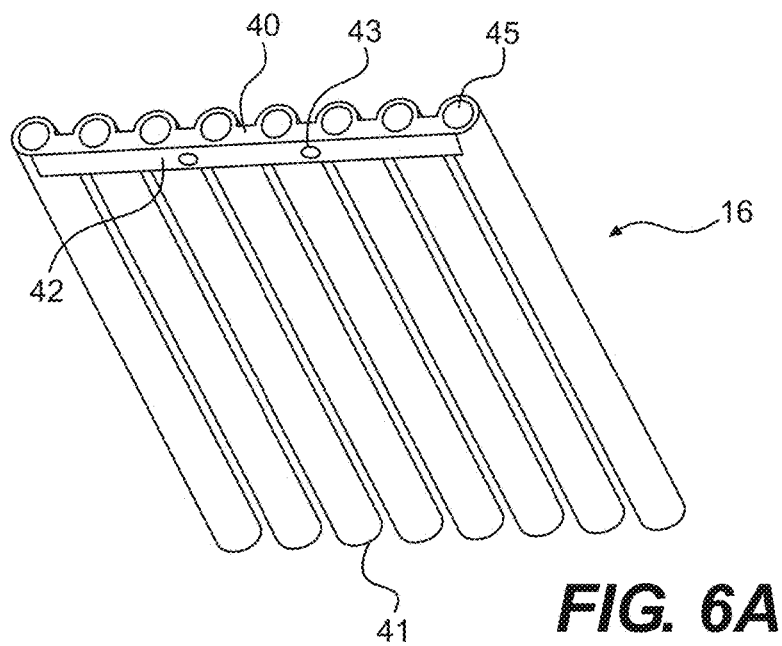
FIG. 6A illustrates multiple outer plugs of a two-part plug system of a cell transplantation device consistent with an embodiment of the present disclosure.

The number of plug systems may correspond to the number of porous chambers 22 in cell transplantation device 10. Outer plug 16 is housed within porous chamber 22 during the device incubation period. In some embodiments, the length of outer plug 16 is approximately equal to the length of the respective porous chamber 22. As illustrated in FIG. 6A, in one embodiment, multiple outer plugs 16 are connected at a proximal end 40 using a common spine 42. Common spine 42 may include one or more grooves 43 to facilitate removal of outer plugs 16 from porous chambers 22. For example, grooves 43 may allow common spine 42 to be grasped using forceps.

Figure 6B:
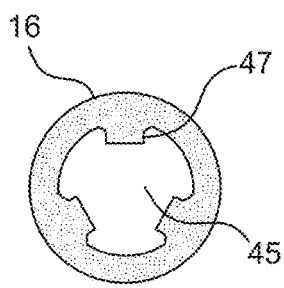
FIG. 6B is a cross-sectional view of an outer plug illustrated in FIG. 6A.

In some embodiments, outer plug 16 has a hollow core 45 that houses an inner plug 18. As shown in FIG. 6B, in one embodiment, hollow core 45 is constrained with one or more internal bosses 47 along the length of the inner surface of the plug. Internal bosses 47 provide an air space between the outer plug 16 and the inner plug 18, which allows trapped air bubbles to escape during the delivery of the cellular preparation, which is described in further detail below. The air space also prevents vacuum formation during the removal of inner plug 18, and thereby, maintains the integrity of the newly formed vascularized collagen matrix in and around the porous chamber. Thus, in some aspects, the plug system comprising outer plug 16 and inner plug 18 may facilitate delivery of cells to the cell transplantation device 10, and may also increase the chances of cell survival within an intact collagen matrix.

Figure 7:
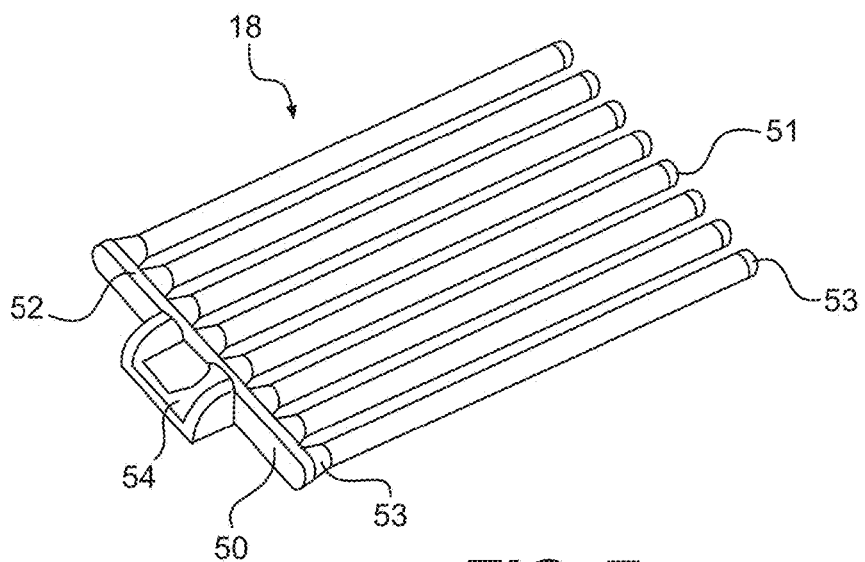
FIG. 7 illustrates multiple inner plugs of a two-part plug system of a cell transplantation device consistent with an embodiment of the present disclosure.

In some embodiments, proximal end 40 and distal end 41 of outer plug 16 comprise sealing mechanisms, for example, internal grooves or tapered surfaces, to ensure an effective seal with inner plug 18. As shown in FIG. 7, proximal end 50 and distal end 51 of inner plug 18 may include complementary sealing mechanisms 53 to prevent infiltration of collagen matrix into hollow core 45 during the incubation period. For example, in one embodiment, sealing mechanism 53 comprises a groove extending around the periphery of the proximal and distal ends of inner plug 18, and outer plug 16 comprises a ridge around the periphery of its distal and proximal ends. In such an embodiment, the ridge on outer plug 16 and the groove on inner plug 18 interlock when inner plug 18 is inserted into the hollow core 45 of outer plug 16, so as to form a complete seal between the inner and outer plugs and prevent permeation of any biological material into hollow core 45. Additionally, in such embodiments, if outer plug 16 comprises one or more internal bosses 47, the height of the ridges at the proximal and distal ends of outer plug 16 may be greater than the height of the internal bosses 47.

Figure 6C:
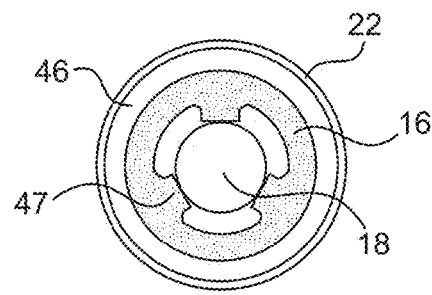
FIG. 6C is a cross-sectional view of a plug system and a single porous scaffold assembly prior to implantation in a host body.
Figure 6D:
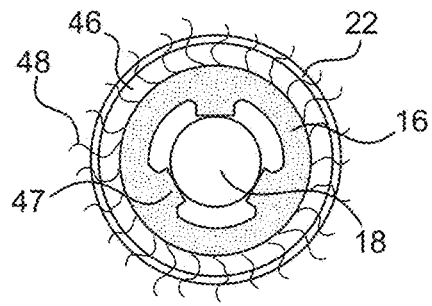
FIG. 6D is a cross-sectional view of the assembly illustrated in FIG. 6C following incubation in a host body.

FIGS. 6C and 6D illustrate cross-sectional views of porous chamber 22 and plug 16, 18 assembly, in accordance with one embodiment of the present disclosure. FIG. 6C is a cross-sectional view of the assembly prior to implantation in a host body, and FIG. 6D illustrates the cross-sectional view of the assembly after incubation in a host body. The inner diameter of porous chamber 22 and outer diameter of outer plug 16 are selected to maintain a space 46 around the periphery of outer plug 16 for tissue formation. For example, in one illustrative embodiment, the inner diameter of porous chamber 22 is no greater than 4.5 mm and the outer diameter of plug 16 is no greater than 3.5 mm. In another embodiment, the inner diameter of porous chamber 22 is no greater than 3.5 mm and the outer diameter of plug 16 is no greater than 2.5 mm. These embodiments provide, for example, approximately 0.5 mm of space around outer plug 16 for formation of a vascularized collagen matrix. The space around outer plug 16 also offers sufficient room for insertion and retraction of the outer plug into and out of the porous chamber.

Figure 6E:
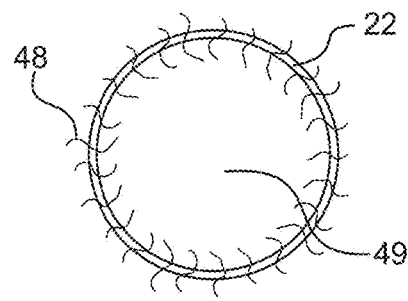
FIG. 6E is a cross-sectional view of a porous scaffold implanted in a host body following removal of the plug system.

When cell transplantation device 10 is implanted in a host body, vascular and connective tissues penetrate through porous chamber 22 into space 46 and form a vascularized tissue matrix 48 around outer plug 16. Plug 16 prevents penetration of tissue matrix 48 further into the lumen of porous chamber 22. When inner plug 18 and outer plug 16 are retracted from porous chamber 22, a pocket 49 is created within porous chamber 22, which may be used for containing cells in the host body. Pocket 49 is enveloped in vascularized tissue matrix 48, as shown in FIG. 6E.

The number of inner plugs 18 may correspond to the number of outer plugs 16. Inner plug 18 is housed within hollow core 45 of outer plug 16 during the device incubation phase. In one embodiment, multiple inner plugs 18 are connected at a proximal end 50 using a common spine 52. In some embodiments, common spine 52 comprises a clip feature 54 to assist in the handling of inner plug 18 during extraction from outer plug 16.

Figure 8:
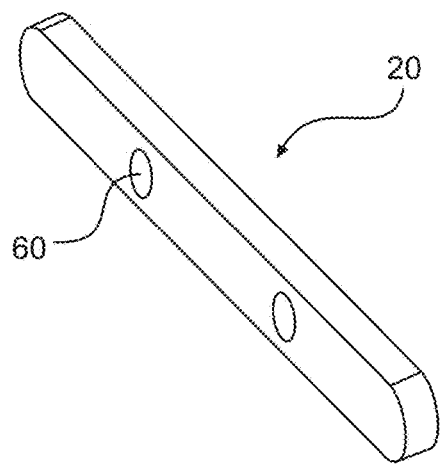
FIG. 8 illustrates a seal for enclosing cells within a vascularized chamber of a cell transplantation device consistent with an embodiment of the present disclosure.

Secondary seal 20, as illustrated in FIG. 8, is used to contain the cellular preparation in the porous chambers when the primary seal 14 is reclosed after delivery of a cell preparation into the cell transplantation device 10. Secondary seal 20 is positioned at proximal end 24 of porous scaffold 12 after the cell preparation is completely delivered into porous chamber 22 and outer plug 16 is retracted from device 10. In some embodiments, secondary seal 20 comprises grooves 60 to facilitate insertion into device 10 using tweezers.

Figure 9A:
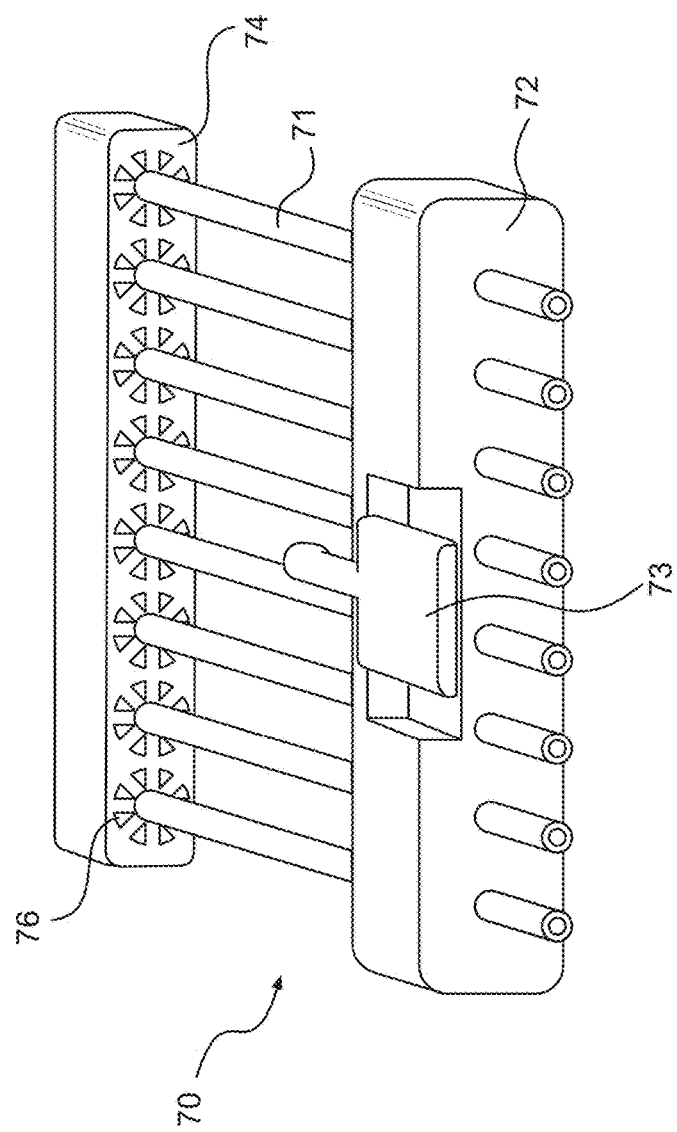
FIG. 9A illustrates a device for delivering cells to a cell transplantation device consistent with an embodiment of the present disclosure.
Figure 9B:
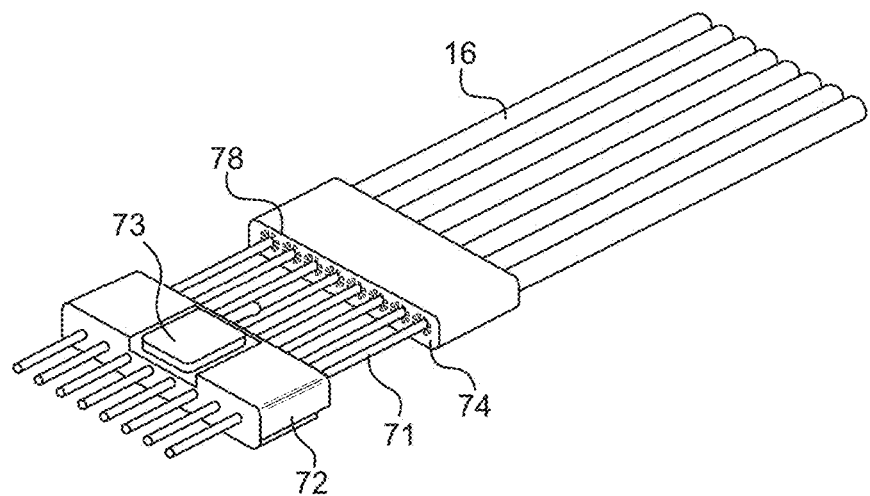
FIG. 9B shows a cell infusion mechanism of the delivery device illustrated in FIG. 9A.

In another aspect of the present disclosure, a device and method for delivering cells into a cell transplantation device are disclosed, and will be explained with reference to cell transplantation device 10. FIG. 9A illustrates the various components of a cell delivery device 70. The cell delivery device 70 comprises at least one cell infusion tube 71, connector cap 72 having a clip feature 73, and connector spacer 74.

Cell infusion tube 71 may comprise polymeric tubing (e.g. polyethylene tubing) or any other suitable material to deliver the cell preparation into porous chamber 22 of device 10 during the cell infusion step. The number of cell infusion tubes in the delivery system may correspond to the number of porous chambers 22.

Connector spacer 74 is positioned at the distal end of cell infusion tube 71 and couples or interfaces with the proximal end 40 of outer plug 16 during the cell delivery process. Connector spacer 74 includes one or more through-holes through which cell infusion tube 71 is inserted, as shown in FIG. 9A. The through-holes are configured to provide a light interference fit with cell infusion tube 71. The fitting is adapted to keep cell infusion tube 71 in place during the cell infusion process. Additionally, in certain embodiments, connector spacer 74 comprises vents 76 to expel air from the air spaces in outer plug 16 created by internal boss 47 during the cell delivery process, as described further below. In one embodiment, outer plug 16 comprises a hub 78 at the proximal end 40. In such an embodiment, connector spacer 74 is inserted into hub 78 during the cell infusion process to secure the delivery device 70 to the cell transplantation device 10.

Figure 9C:
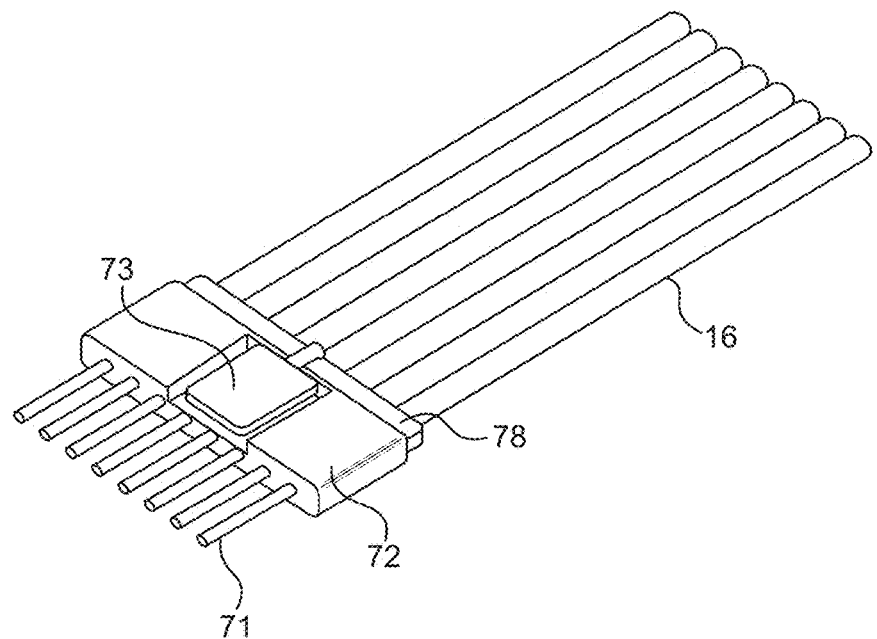
FIG. 9C shows additional steps of the cell infusion mechanism of the delivery device illustrated in FIGS. 9A-9B.

The proximal end of cell infusion tube 71 comprises connector cap 72. As the tube is inserted into outer plug 16, connector cap 72 advances distally towards connector spacer 74. When tube 71 is completely inserted into outer plug 16, connector cap 72 fits over connector spacer 74 and/or hub 78, and clip feature 73 connects with outer plug 16/or hub 78 along common spine 42, as shown in FIG. 9C. This enables connector cap 72, connector spacer 74, and outer plug 16 to be retracted as a single unit as the cell preparation is infused into porous chamber 22.

In yet another aspect of the present disclosure, a method for cellular transplantation is disclosed and will be explained with reference to cell transplantation device 10 and cell delivery device 70. The cell transplantation method is not limited to the device embodiments disclosed herein and may be used with any cell transplantation and cell delivery devices.

FIG. 10 is a flowchart illustrating the steps of an exemplary cell transplantation procedure. The cell transplantation procedure is generally a two-step process comprising a device implantation step followed by a cell infusion step. Device 10 is implanted in the host body prior to delivery of cells to allow adequate time for collagen and blood vessels to infiltrate porous scaffold 12. In some embodiments, device 10 is sterilized using ethylene oxide prior to implantation. The device 10 may be packaged in a self-seal package or any other sterilizable package along with a sterility indicator strip for an ethylene oxide-based sterilization process. In some other embodiments, gamma radiation or dry heat autoclaving is used to sterilize the device prior to implantation. The type of sterilization method used is dependent on the scaffold material, since dry heat autoclaving is known to warp certain polymeric materials (e.g. polypropylene) due to low heat deflection temperature. Gamma radiation, at a sterilization dose of 6 M-Rad, can successfully sterilize cell implantation devices; however, gamma radiation may decrease the shelf life of devices made of polypropylene.

Device 10 may be implanted subcutaneously or intraperitoneally. For example, for subcutaneous implantation of the device in the host body, an incision is made through the dermis and epidermis followed by careful blunt dissection of connective tissue and adipose, creating a subcutaneous pocket caudal to the incision line (step 810). Once an adequate space is created (roughly the dimensions of the device), device 10 is implanted into the subcutaneous pocket, and the incision is sutured (step 820). Alternatively, device 10 may be implanted in the peritoneal cavity through an abdominal incision. The device implantation steps (steps 810 and 820) are followed by a device incubation period (step 830) during which a vascularized collagen matrix is deposited in and around porous scaffold 12.

After the incubation period, device 10 is accessed through a second surgical incision. For example, proximal end 31 of primary seal 12 may be trimmed in situ to open device 10 (step 840). Inner plug 18 is then extracted from outer plug 16 and discarded (step 850). During the inner plug removal process, air movement is facilitated by internal bosses 47, which prevent formation of a vacuum inside the device, which can cause disruption of any newly formed blood vessels in and around the device. Removal of inner plug 18 disengages proximal end 50 and distal end 51 of inner plug 18 from proximal end 40 and distal end 41 of outer plug 16. A cellular preparation is then delivered into device 10 using cell delivery device 70.

Figure 11A:
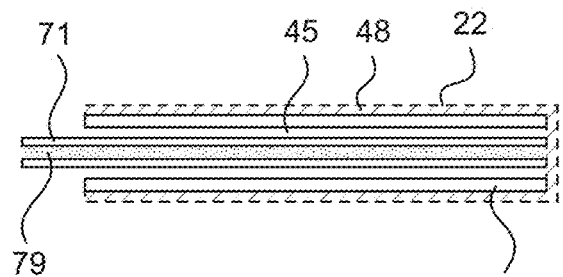
FIGS. 11A-11D show a schematic overview of certain steps of a cell infusion procedure in accordance with the present disclosure.

FIGS. 11A-11D show a schematic overview of certain steps of an exemplary cell infusion procedure and will be explained with reference to the flowchart shown in FIG. 10. For administering the cells into device 10, cell infusion tube 71 of delivery device 70 is loaded with cellular preparation 79, and the tube is inserted into the hollow core 45 of outer plug 16, as shown in FIG. 11A (step 860). Connector spacer 74 couples with the proximal end 41 and/or hub 78 of outer plug 16. As tube 71 is advanced into the outer plug, air is vented through internal bosses 47 of outer plug 16 and vents 76 of connector spacer 74. When tube 71 is advanced all the way into outer plug 16, connector cap 72 interfaces with connector spacer 74. Clip 73 of connector cap 72 is then connected to hub 78 of outer plug 16 (step 870). In this case, outer plug 16, connector cap 72 and connector spacer 74 are then retracted slightly from porous chamber 22 as a single unit to create a space at the distal end of porous chamber 22 (step 875). In some embodiments, outer plug 16 may be retracted slightly from porous chamber 22 prior to connecting delivery device 70 with outer plug 16. In other words, step 875 may be performed prior to step 870. Gentle pressure is applied to a syringe connected to cell infusion tube 71 to deliver the cells into porous chamber 22 (step 880). Care is taken to ensure tube 71 remains in the porous chamber 22 as pressure is applied to deliver the cellular preparation.

Figure 11B:
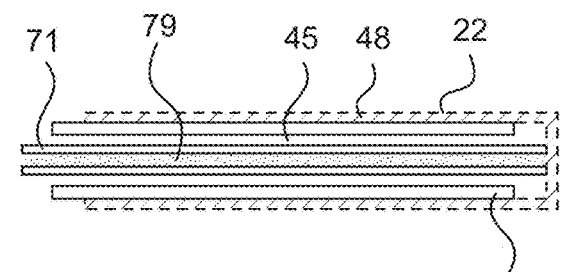
Figure 11C:
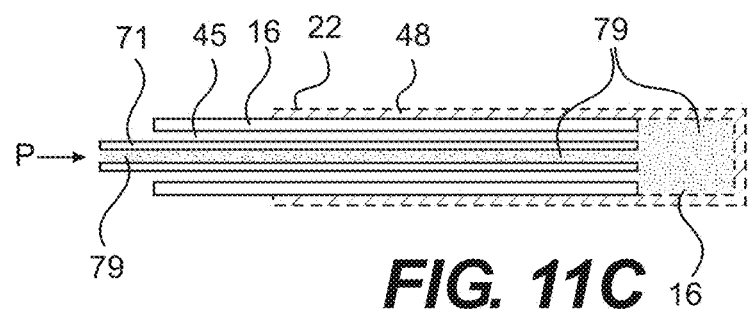
Figure 11D:
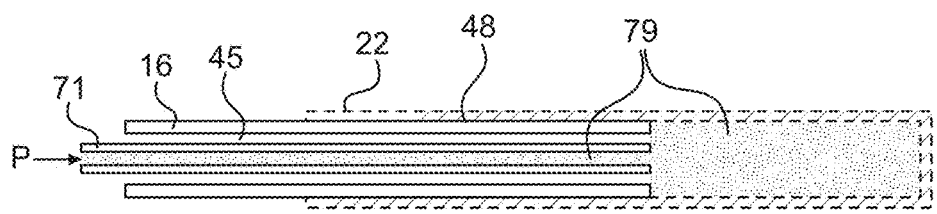

In one embodiment, outer plug 16 is retracted approximately 5 mm before the cell infusion is started, as illustrated in FIG. 11B. As pressure (P) is applied to the syringe connected to cell infusion tube 71, the cell preparation 79 infuses into the porous chamber 22. As the cell preparation is delivered into porous chamber 22, outer plug 16 and cell infusion tube 71 are withdrawn from the device, as shown in FIGS. 11C and 11D (step 885). When the device is completely filled with the cellular preparation 79, cell infusion is stopped and cell infusion tube 71 is completely retracted from device 10 (step 890). Porous chamber 22 is then evaluated for remaining capacity for cellular preparation, and any remaining cell preparation may be carefully added to the end of the porous chamber. The cell preparation is contained within the porous chamber 22 by placing secondary seal 20 at the proximal end 40 of porous chamber 22, followed by closing the re-sealable lock 34 of primary seal 12, and securing the proximal end 31 of primary seal 12 with surgical sutures or staples or other suitable sealing mechanisms (step 895). Finally, the surgical incision is closed using surgical sutures, staples or tissue adhesives, thereby completing the cell transplantation procedure.

The devices and methods for cell transplantation disclosed can be used for transplantation of any therapeutic cells, or a combination of cells, into a host body for providing therapeutic biological material to the host for the treatment of a disease condition. The cells may be allogeneic, xenogeneic or syngeneic donor cells, patient-derived cells, including stem cells, cord blood cells and embryonic stem cells. The stem cells may be differentiated into the appropriate therapeutic cells. The cells may be immature or partially differentiated or fully differentiated and mature cells when placed into the device. The cells may also be genetically engineered cells or cell lines. In one aspect, an embodiment consistent with the present disclosure is used for transplantation of islets of Langerhans cells to provide means for blood glucose regulation in the host body. In another aspect, an embodiment of a cell transplantation device is used for co-transplantation of islets of Langerhans and Sertoli cells, where the Sertoli cells provide immunological protection to the islet cells in the host body. The immune protection provided by Sertoli cells in a host body was previously disclosed, for example, in U.S. Pat. No. 5,725,854, which is incorporated herein by reference in its entirety. Accordingly, this disclosure also contemplates methods of treating various diseases by transplanting therapeutic amounts of cells to subjects in need thereof using an embodiment of a cell transplantation device as disclosed here.

The density of the transplanted therapeutic cells, or combinations of cells, is determined based on the body weight of the host and the therapeutic effects of the cells. As noted earlier, the dimensions of the cell transplantation device and number of porous chambers to be used (in a multi-chamber device) are determined based on the number of the cells required, the extent of vascularization achievable during the device incubation period, and the diffusion characteristics of nutrients and cellular products in and out of the implanted devices.

EXAMPLES

The following examples are provided to better explain the various embodiments and should not be interpreted in any way to limit the scope of the present disclosure. The cell transplantation devices used in these examples are formed of polypropylene meshes and comprise a single PTFE plug in each porous chamber of the devices.

1. Cell Transplantation Devices Containing Islet Cells Are Capable of Restoring Normoglycemia in Lewis Rats Cell transplantation devices were used for implanting syngeneic islet cells in Lewis rats for restoring normoglycemia. The glucose response of the implanted cells was compared with the glucose response of islet cells administered directly into the portal veins of rats. The Lewis rats were divided into three study groups, with nine rats in each group. In the first and second study groups, the devices were implanted in intraperitoneal and subcutaneous cavities, respectively. In the third group, the islet cells were administered directly into the portal veins.

The implanted devices were incubated in the Lewis rats for at least one month to allow vascular ingrowth. Diabetes was then chemically induced in the rats by injecting streptozotocin. The rats were considered diabetic if three successive blood glucose readings were at least 18.0 mM. Isolated Lewis rat islet cells (10,000 IEQ/Kg weight) were then infused into the implanted devices or directly into the portal veins of diabetic rats. Insulin pellets were removed at 14 days post islet transplantation (denoted by the closed rectangle above the graphs in FIGS. 11A and 11B). Blood glucose levels in the rats were monitored for a period of 100 days. At 100-days post-transplantation, the devices were removed to confirm that the transplanted islets were responsible for reversal of diabetes.

Figures 12A, 12B:
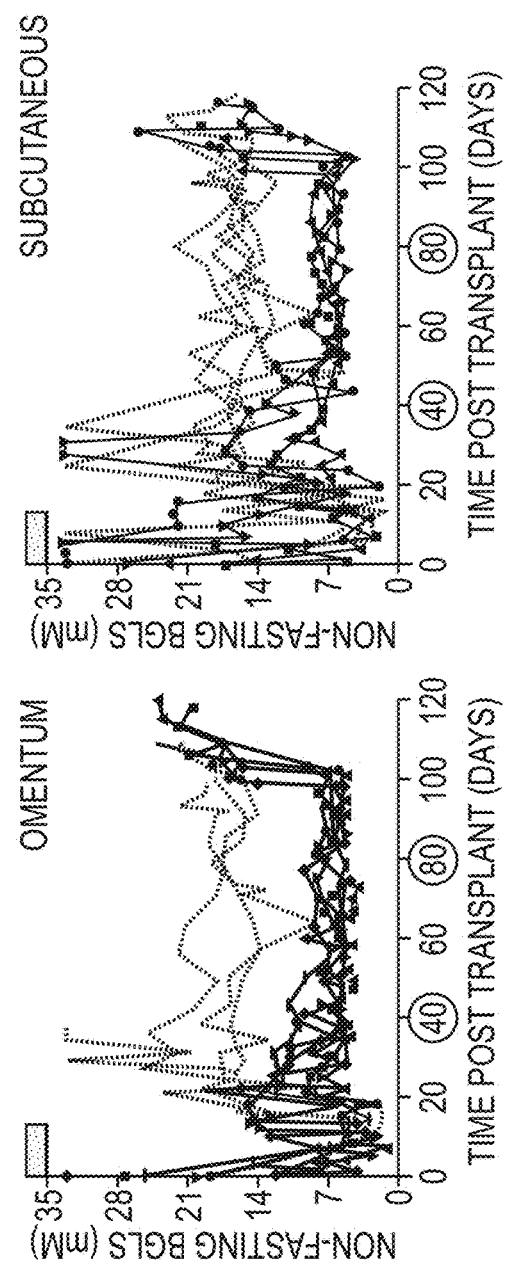
FIG. 12A shows line graphs of blood glucose measurements after intraperitoneal implantation of cell transplantation devices, as described in Example 1.
FIG. 12B shows line graphs of blood glucose measurements after subcutaneous implantation of cell transplantation devices, as describe in Example 1.

FIGS. 12A and 12B show glucose normalization results for rats receiving intraperitoneal (omental chamber) and subcutaneous cell transplantation devices, respectively. Successful cell transplantation resulted in normalization of blood glucose levels (glucose reading less than 8.0 mM), as denoted by the solid traces. The transplants not achieving normoglycemia are denoted by dotted traces. The results indicate that normal glycemic level was maintained in a statistically significant number of diabetic rats that received the islet cells. Following the removal of the implanted devices at 100-days post-transplantation, rats which previously demonstrated normal glycemic levels returned to hyperglycemic levels, indicating that the devices contained fully functioning grafts that were responsible for achieving normoglycemia prior to device removal. The rate at which blood glucose concentrations reached non-diabetic levels was statistically different between the study groups ($p<0.0001$, t-test).

Figure 12C:
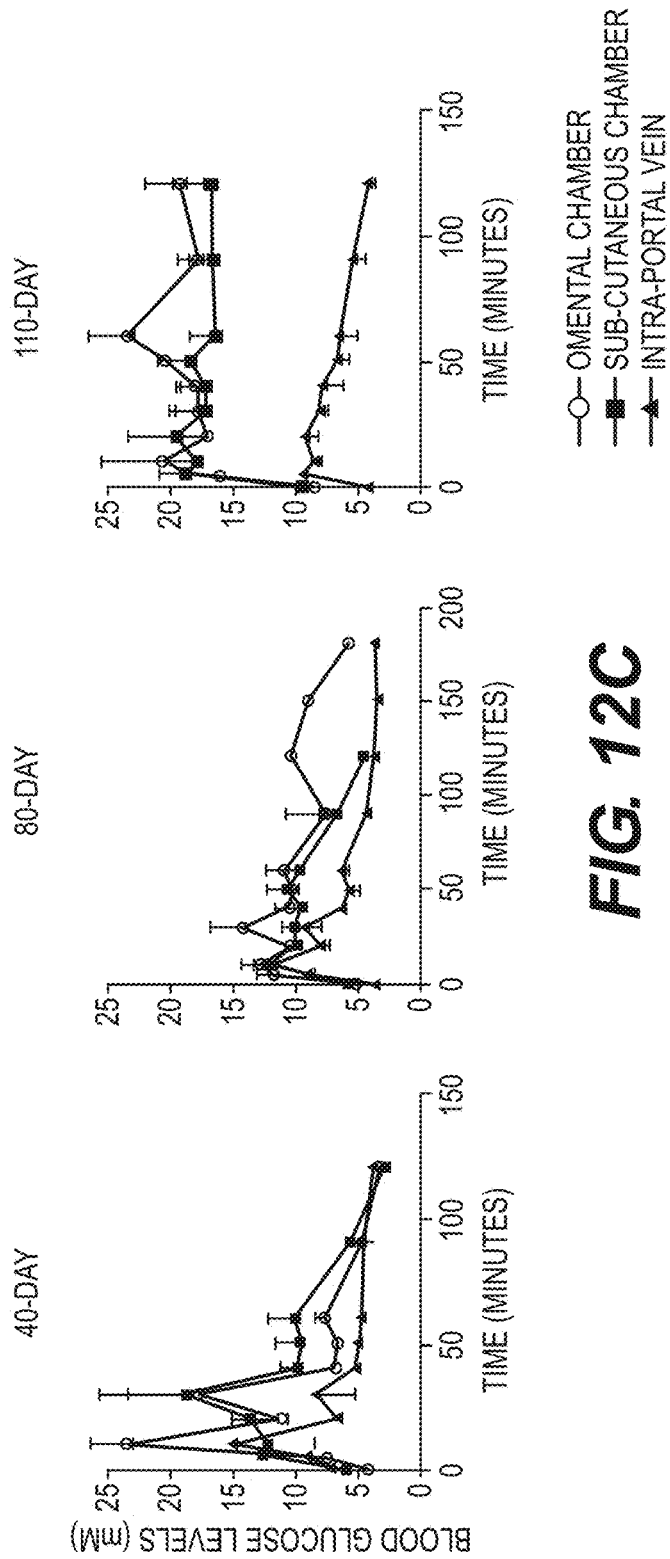
FIG. 12C shows line graphs of IVGTT responses in Lewis rats transplanted with islet cells at 40 days post-transplant, 80 days post-transplant and post-device removal (at 110 days post-transplant), as described in Example 1.

FIG. 12C shows IVGTT (intravenous glucose tolerance test) responses in Lewis rats transplanted with islet cells. IVGTTs was performed at 40 days and 80 days post-transplantation The glucose response of rats with intraperitoneal and subcutaneous transplants were compared against glucose response of rats that received intra-portal islet cells. IVGTTs were performed on three rats in each study category. At 40-days and 80-days post transplantation, the blood glucose levels in rats transplanted with islet cells dropped below 8.0 mM within 50 minutes of receiving a glucose challenge, as shown in FIG. 12C. The cell transplantation devices were removed at 100-days. The blood glucose levels did not drop when a bolus of glucose was administered at 110-days, indicating that the transplanted islet cells were responsible for the normoglycemia achieved in the diabetic rats prior to removal of the implanted devices.

Figure 12D:
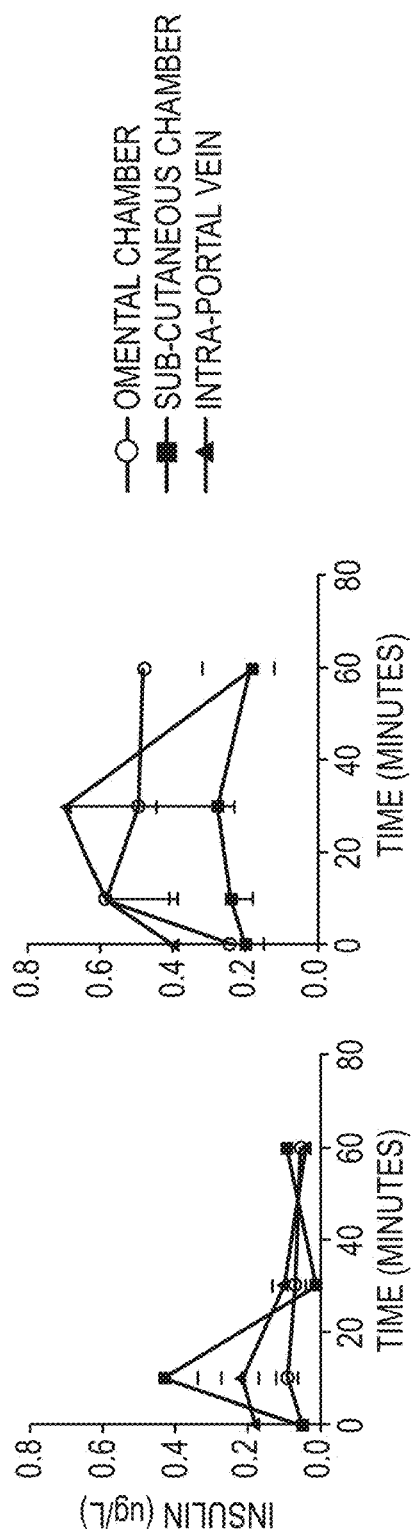
FIG. 12D shows line graphs of insulin levels in response to glucose challenge in Lewis rats transplanted with islet cells, as described in Example 1.

FIG. 12D show insulin responses in Lewis rats transplanted with islet cells. The insulin levels were tested using enzyme linked immunosorbent assays (ELISA). The analysis was performed in triplicate. The results indicate a significant difference in blood insulin levels upon glucose challenge ($p<0.005$, t-test). As shown in FIG. 12D, the insulin levels in rats that received the transplanted devices correlated well with the insulin levels in rats that received intra-portal islet cells.

Figure 13A:
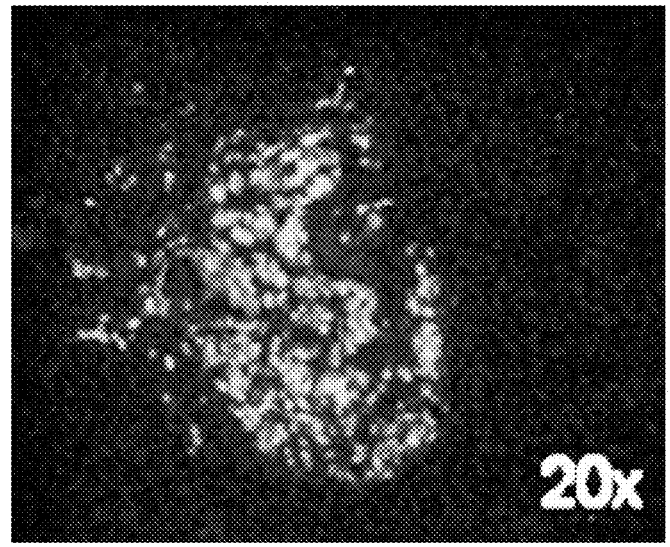
FIG. 13A demonstrates histological staining of insulin within the chamber of an implanted device, as described in Example 2.

2. Histological Detection of Insulin and Vascularization Within the Porous Chambers of Cell Transplantation Devices Following removal of the implanted devices at 100-days, insulin was detected in the devices using specific primary antibodies against insulin. FIG. 13A shows the result of the insulin staining within the porous chamber of a subcutaneously implanted device. The detection of insulin within the chamber indicated that the islet cells contained in the devices were viable and functional at 100-days post-transplantation.

Figure 13B:
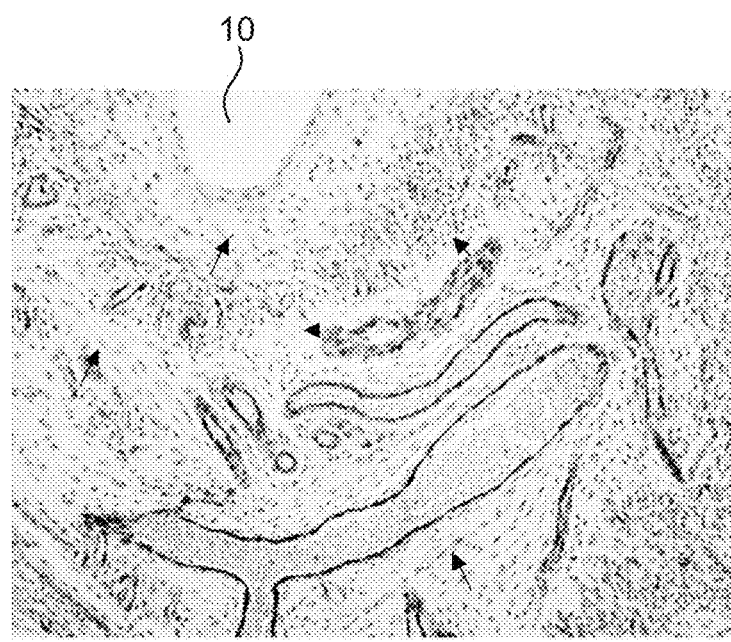
FIG. 13B demonstrates histological staining of vascularization (microvasculature) within the chamber of an implanted device, as described in Example 2.

Histological evaluation of implanted devices was also performed to verify the formation of vascular tissue in the collagen matrix deposited in and around the devices. Immunohistochemical staining for Factor VIII associated with endothelial cells indicated well-formed vascular structures deeply embedded in connective tissue, as shown in FIG. 13B (dark structure indicates endothelium; cell nuclei are indicated by arrows). The histological evaluation also demonstrated the penetration of neovascularized tissue towards the core of the cell transplantation devices.

3. Assessment of Angiogenesis and Collagen Deposition in Cell Transplantation Devices To determine the appropriate length of the implantation phase (time between implantation of device and engraftment of islets), cell transplantation devices were implanted subcutaneously into eight week old Yorkshire-Landrace pigs for 2, 4 and 8 weeks. Following implantation for the respective time period, the devices were explanted and analyzed to determine the level of angiogenesis and collagen deposition.

a) Gross Assessment of Angiogenesis and Collagen Deposition

Photographs were taken of both the ventral and dorsal surfaces of the explanted devices for gross analysis of blood vessel and tissue formation. A 1 cm×1 cm grid was laid over the photographs to quantify the microvessel and tissue (collagen with cells) formation. Each 1 $cm^2$ box within the grid was scored for vessel formation, allowing for a total vessel/$cm^2$ to be calculated for the entire surface of the explanted devices. The average thickness on the medial and lateral perimeters of the devices were measured to evaluate the amount of collagen deposition. FIG. 14 shows a table of the average collagen thickness and total blood vessel/$cm^2$ calculated for four devices formed using different porous materials (meshes). Sufficient microvessel and tissue formation was observed for all the four mesh types at 2 weeks post-implantation. The results also indicate that the amount of time required for microvessel formation and collagen deposition may vary depending on the device material (porosity, surface roughness, etc. of the meshes).

b) Histological Analysis of Angiogenesis and Collagen Deposition

Figure 15A:
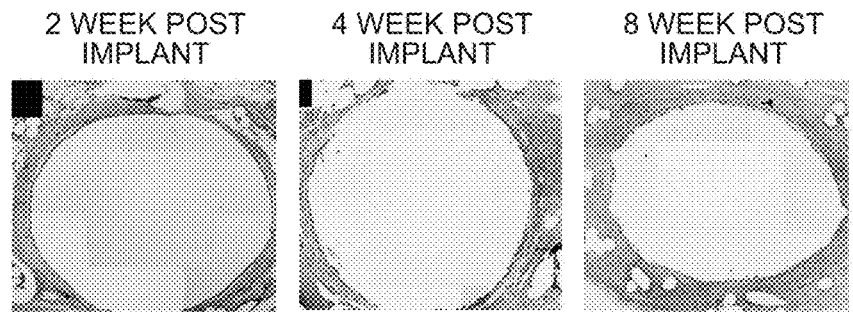
FIG. 15A demonstrates tissue incorporation into a cell transplantation device at 2, 4 and 8 weeks after implantation, as described in Example 3.
Figure 15B:
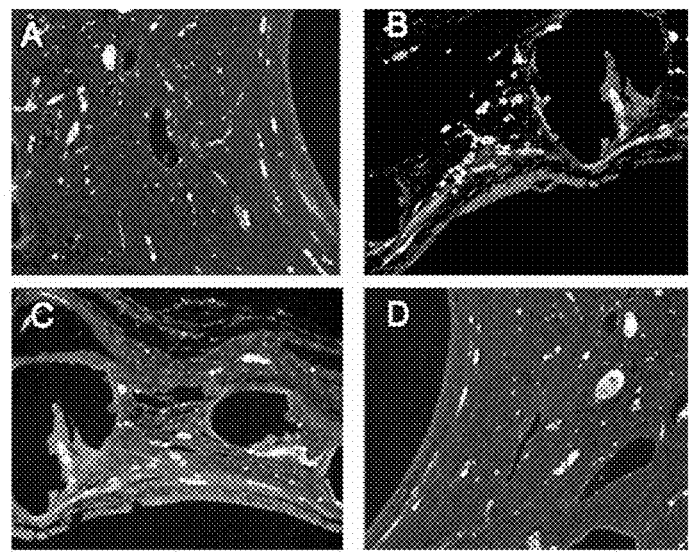
FIG. 15B shows blood vessel formation at various margins of an implanted device prior to cell transplantation, as described in Example 3.

Angiogenesis was determined by staining endothelial cells with Hematoxylin and Eosin (H&E) stain (FIG. 15A) and von Willebrand factor (FIG. 15B). FIG. 15A demonstrates tissue incorporation into the devices at 2, 4 and 8 weeks after implantation. FIG. 15B shows blood vessel formation at various margins of a device prior to cell transplantation. The assessment of tissue incorporation into the devices showed that the devices incorporate collagen and microvessels at all measured time points prior to islet transplantation.

4. Assessment of Cell Transplantation Devices Receiving Porcine Autograft Islets Eight week old Yorkshire-Landrace pigs were implanted with cell transplantation devices for four and eight weeks. To make the animals diabetic, a 90% pancreatectomy was performed followed by a 150 mg/Kg intravenous dose of streptozotocin one day after the surgery. Islets were isolated from the pancreas before performing the pancreatectomy. The immature islet grafts were transplanted into the animals five days after graft isolation and pancreatectomy to allow sufficient time for recovery and confirmation of diabetes.

Figure 16:
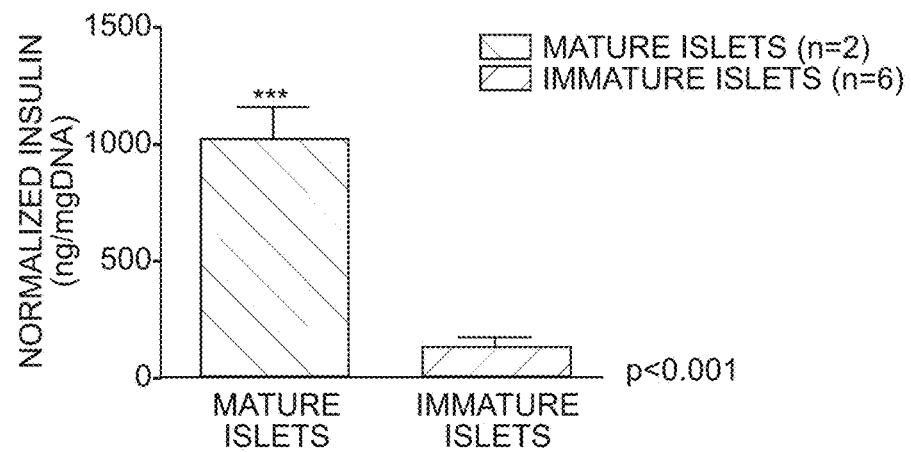
FIG. 16 shows bar graphs of levels of insulin produced by mature and immature islets, as described in Example 4.

The insulin producing capacities of the immature islet cells were tested prior to transplantation. As shown in FIG. 16, the immature islets produced about 10% of the insulin normally expected from adult islets. This fact combined with the low islet transplant number of about 3-5K IEQ/Kg (5-10% of insulin producing islets normally used in intra-portal transplants) provides a rigorous test of the cell transplantation devices. Currently in clinical islet transplantation therapy, the infusion of an adequate amount of β-cell mass has posed an obstacle for treatment of insulin-dependent diabetes. Insulin independence is routinely achieved when a sufficient quantity of islet cells are delivered, approximately 10,000 IEQ/Kg of recipient's body weight. To provide this quantity of islet cells, present day islet transplant protocols require more than one donor pancreas per recipient, creating a strain on an already limited donor supply. Therefore, if glycemic control can be achieved using only 5-10% of the islets currently used in intra-portal transplants, the number of diabetic patients that could receive islet transplant therapy would increase significantly.

Histological analyses of explanted devices were performed to test the long-term survival and function of transplanted islets. Islet graft function was also monitored through bi-weekly blood glucose and bi-monthly intravenous glucose tolerance tests (IVGTTs).

a) Histological Analysis of Islet Graft Function

Figure 17A:
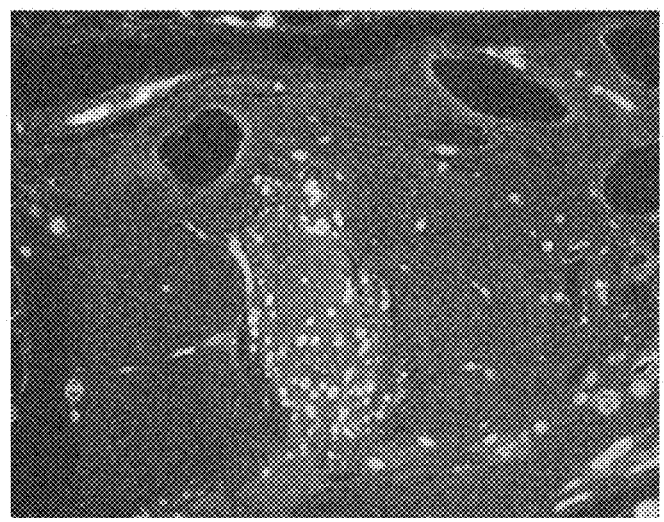
FIG. 17A demonstrates histological staining of insulin and microvasculature within the chamber of an implanted device, as described in Example 4.
Figure 17B:
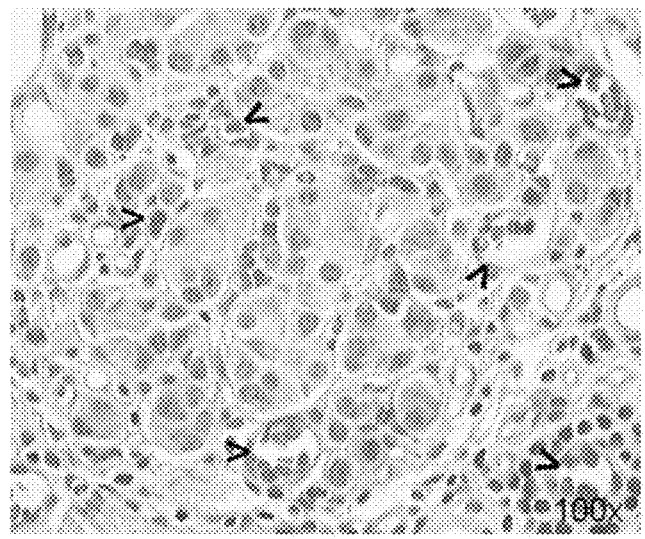
FIG. 17B demonstrates histological staining of microvasculature within the chamber of an implanted device after cell transplantation, as described in Example 4.

Following explantation of the devices at 9-weeks, insulin was detected in the devices using specific primary antibodies against insulin. FIG. 17A shows the result of the insulin staining within the porous chamber of an explanted device. The detection of insulin within the chamber indicated that the islet cells contained in the device were viable and functional at 9-weeks post-transplantation. Immunohistochemical staining of explant sections demonstrated healthy, well-configured islets surrounded by robust microvessels (FIG. 17B, microvessels indicated by arrows).

b) Blood Glucose Measurements

Weekly fasting and non-fasting blood glucose levels were measured to monitor for islet graft function following transplantation. These measurements aid in determining the overall efficacy of the cell transplantation devices in long-term control of blood glucose levels. Fasting blood glucose readings provide a controlled measure of graft function. Briefly, a drop (several microliters) of blood is collected from a vein of a recipient animal, and the blood glucose level is determined using a Freestyle Lite glucometer or other glucose testing device.

Figure 18:
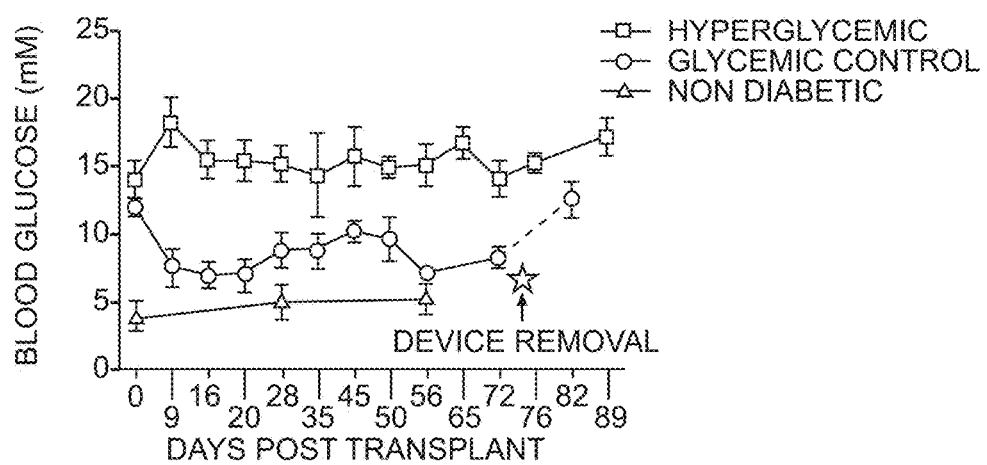
FIG. 18 shows line graphs of blood glucose levels following islet autograft transplantation, as described in Example 4

As shown in FIG. 18, the transplanted islets demonstrated long-term glucose control up to the explantation of the devices at 72 days. The animals in the "glycemic control" group (n=4) were insulin-independent, and the blood glucose levels were controlled by the islets in the cell transplantation devices alone. The animals in this group showed long-term insulin independence after islet transplantation. Some animals, however, remained hyperglycemic (elevated daily blood glucose levels) following transplantation of islets into the devices (n=6). This was related to poor metabolic quality of the pre-transplant islets and low islet transplant dose (IEQ/Kg). The quality of islets prior to transplantation correlated well with long-term islet function.

c) Glucose Tolerance Test

Glucose tolerance tests are important in assessing islet graft function through the comparison of pre- and post-transplant IVGTT results. To test the efficacy of the cell transplantation devices, IVGTTs were conducted prior to pancreatectomy (baseline), at various time points after islet transplantation into the devices, and after explantation of the devices. IVGTT was performed by injecting a dose of dextrose and measuring the time it takes for endogenous insulin to bring the glucose levels to baseline. In addition to measuring blood glucose level, blood was sampled at various time points to measure the level of C-peptide, which is a by-product created when insulin is produced by β cells. Results for an IVGTT were interpreted using absolute values of blood glucose level (FIG. 19A), area under curve (AUC) of blood glucose level (FIG. 19B), and fold change in C-peptide level (FIG. 19C).

Figure 19A:
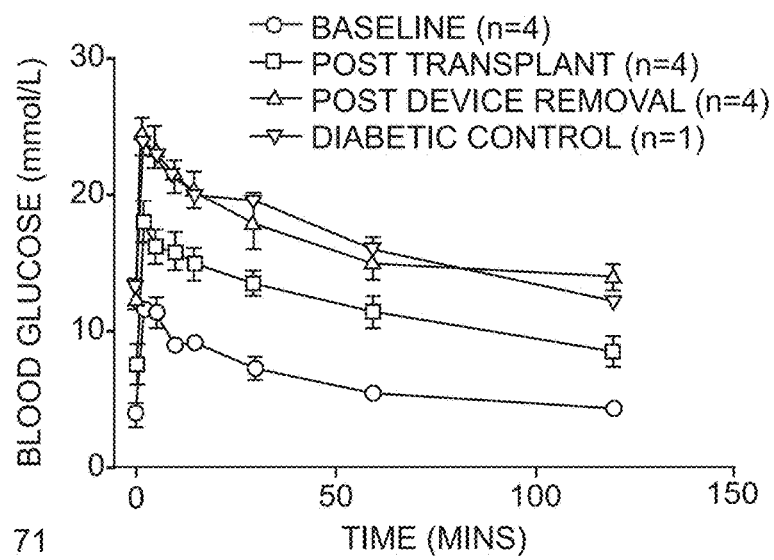
FIG. 19A shows line graphs of absolute blood glucose levels in response to glucose challenge in Yorkshire-Landrace pigs transplanted with islet cells, as described in Example 4.
Figure 19B:
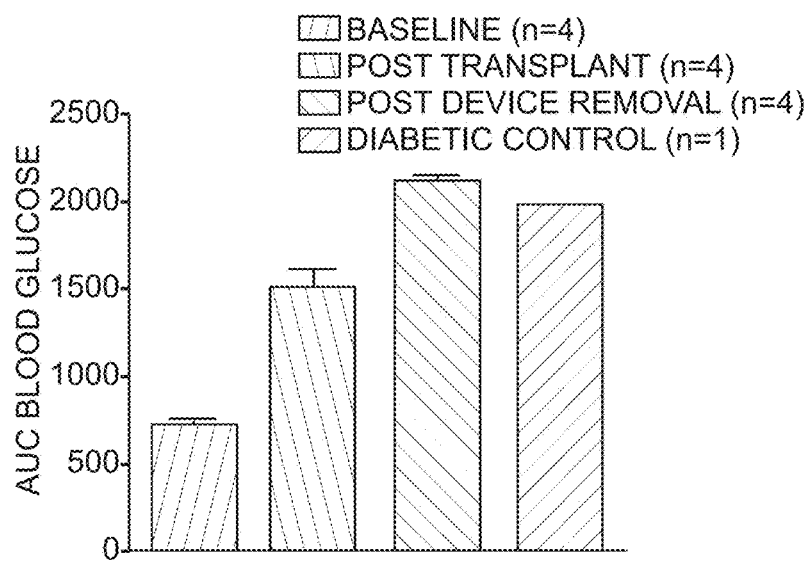
FIG. 19B shows bar graphs of Area Under the Curve (AUC) for blood glucose levels in response to glucose challenge in Yorkshire-Landrace pigs transplanted with islet cells, as described in Example 4.
Figure 19C:
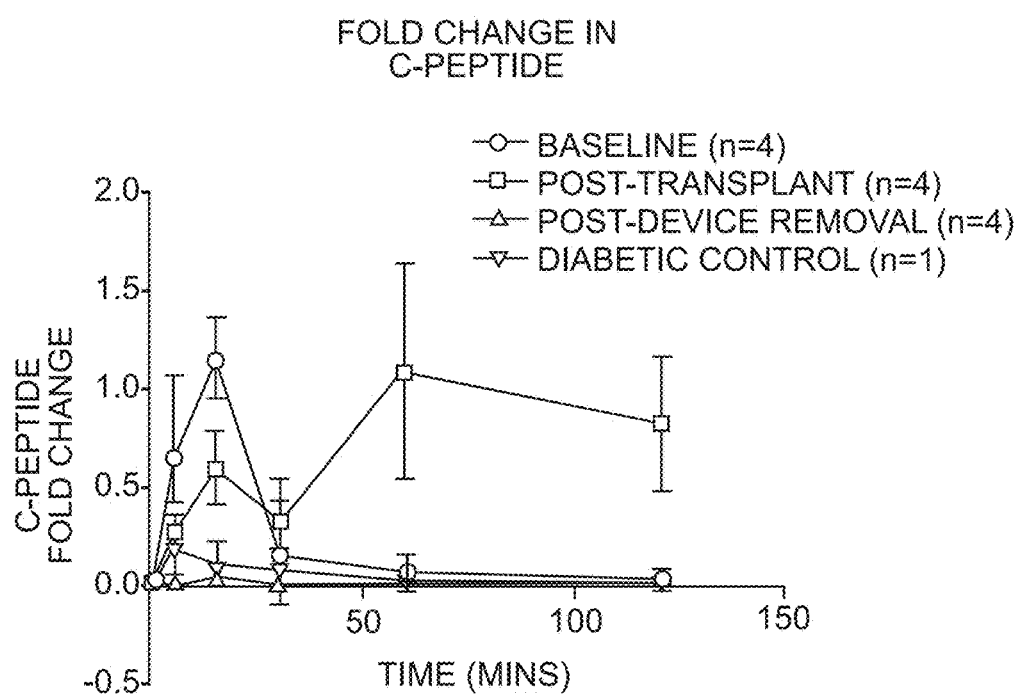
FIG. 19C shows line graphs of fold change in C-peptide levels in response to glucose challenge in Yorkshire-Landrace pigs transplanted with islet cells, as described in Example 4.

As shown in FIGS. 19A and 19B, the glucose levels rise significantly ($p<0.001$, Anova) after the device is explanted, indicating that the removal of the device results in elimination of insulin function similar to a diabetic animal with no islets. While the lowest glucose levels were detected in non-pancreatectomized animals, the islet autograft recipients showed significant reduction is glucose levels after dextrose injection, indicating that the immature islets can survive and function after transplantation.

Serum samples from the IVGTTs were analyzed using Linco's Porcine C-Peptide Radioimmunoassay kit, which utilizes an antibody made specifically against synthetic porcine C-peptide. Serum samples at 0, 5, 15, 30, 60 and 120 minutes post-dextrose injection were analyzed for the presence of porcine C-peptide. Four study groups were tested—non-pancreatectomized pigs (baseline), islet autograft recipients (post-islet transplantation), autograft recipients that have had their devices removed (post-device removal) and diabetic control pigs. When examining fold changes in C-peptide levels among the different study groups, baseline and post-islet transplant recipients showed very comparable result, although the C-peptide level in post-islet transplant recipients increased at 60 minutes as opposed to 30 minutes for the baseline group (FIG. 19C). Furthermore, fold changes in C-peptide for the post-device removal group and diabetic control group were similar, indicating that the transplanted islets were responsible for C-peptide release prior to device removal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A device for implanting cells in a host body, comprising:
    a porous scaffold comprising a polymer mesh forming the walls of at least one chamber, wherein the chamber comprises an opening at either or both of a proximal end and a distal end of the chamber, wherein the proximal end and the distal end are separated by a lumen that is bounded by the walls, and wherein the porous scaffold has pores sized to facilitate growth of vascular and connective tissues around and through the walls of the at least one chamber;
    at least one removable, non-porous two-plug system configured to be positioned within the lumen of the at least one chamber, wherein the two-plug system comprises an outer plug configured to be positioned within the lumen of the at least one chamber and an inner plug configured to be positioned within the outer plug, and wherein the two-plug system extends along the lumen of the chamber;
    at least one seal configured to enclose either or both the proximal end and the distal end of the chamber; and
    cells within the chamber.

2. The device of claim 1, wherein the cells are further encapsulated in alginate, a polysaccharide hydrogel, chitosan, calcium or barium alginate, a layered matrix of alginate and polylysine, photopolymerizable poly(ethylene glycol) polymer, a polyacrylate, hydroxyethyl methacrylate, methyl methacrylate, a silicon capsule, a silicon nanocapsule, a polymembrane, or acrylonitrile-co-vinyl chloride.

3. The device of claim 1, wherein the cells comprise islets of Langerhans.

4. The device of claim 1, wherein the cells comprise islets of Langerhans and Sertoli cells.

5. The device of claim 1, wherein the cells comprise stem cells.

6. The device of claim 1, wherein the cells comprise differentiated stem cells, and wherein the differentiated stem cells are derived from neural stem cells, cord blood cells, embryonic stem cells, or mesenchymal stem cells.

7. The device of claim 1, wherein the cells are genetically engineered cells or cell lines.

8. The device of claim 1, wherein the porous scaffold comprises multiple chambers that are connected laterally.

9. The device of claim 1, wherein the at least one seal is a polymer film that is ultrasonically welded to the porous scaffold.

10. The device of claim 1, wherein the outer plug and the inner plug comprise complementary sealing mechanisms.

11. The device of claim 1, wherein the inner wall of the outer plug comprises at least one protrusion along the length of the outer plug.

12. The device of claim 1, wherein the porous scaffold is configured to facilitate growth of vascular and connective tissues into the porous chamber to encapsulate the two-plug system in a neovascularized collagen matrix, and wherein the two-plug system is capable of being withdrawn from the chamber to create a space within the chamber that is encapsulated in the neovascularized collagen matrix.

13. The device of claim 1, further comprising a cell delivery device comprising at least one cell infusion tube configured to be positioned within the outer plug and configured to deliver cells to the chamber of the device.

14. The device of claim 13, wherein the cell delivery device further comprises a connector configured to connect to the outer plug when the at least one cell infusion tube is inserted into the outer plug, and optionally wherein the connector comprises a clip for connecting to the outer plug and optionally wherein attachment of the connector to the outer plug allows the connector and the outer plug to be retracted from the device as a single unit.

15. The device of claim 1, wherein the porous scaffold comprises one chamber, two chambers, three chambers, four chambers, five chambers, six chambers, seven chambers, eight chambers, ten chambers, twelve chambers, or more chambers.

16. The device of claim 1, further comprising a material coating at least a part of the porous scaffold, wherein the material stimulates tissue incorporation and angiogenesis.

17. The device of claim 1, wherein the cells comprise two or more cell types selected from the group consisting of islets of Langerhans, Sertoli cells, stem cells, differentiated stem cells, neural stem cells, dopaminergic neurons, cord blood cells, embryonic stem cells, and mesenchymal stem cells.

18. The device of claim 16, wherein the material comprises a biocompatible, biodegradable material, a non-biodegradable material, or a combination thereof.

19. The device of claim 1, wherein the polymer mesh comprises a polytetrafluoroethylene mesh, a polyurethane mesh, a polyester mesh, and/or a silk mesh.

20. The device of claim 16, wherein the material comprises one or more of a growth factor, an antifibrotic agent, a polymer, vascular endothelial growth factor (VEGF), collagen, fibronectin, polyethylene-imine and dextran sulfate, polyvinyl siloxane and polyethyleneimine, phosphorylcholine, poly(ethylene glycol), poly(lactic-co-glycolic acid), poly(lactic acid), polyhydroxyvalerate and copolymers, polyhydroxybutyrate and copolymers, polydiaxanone, polyanhydrides, poly(amino acids), poly(orthoesters), gelatin, a cellulose polymer, a chitosan, an alginate, vinculin, agar, agarose, hyaluronic acid, and matrigel.

21. A method for transplanting cells into a host body, comprising implanting the device of claim 1 into the host.

22. The method of claim 21, further comprising the step of imaging the porous scaffold prior to delivering cells.

23. A device for implanting cells in a host body, comprising:
a porous scaffold comprising a polymer mesh forming the walls of at least one chamber, wherein the chamber comprises an opening at either or both of a proximal end and a distal end of the chamber, wherein the proximal end and the distal end are separated by a lumen that is bounded by the walls, and wherein the porous scaffold has pores sized to facilitate growth of vascular and connective tissues around and through the walls of the at least one chamber;
at least one removable, non-porous two-plug system configured to be positioned within the lumen of the at least one chamber, wherein the two-plug system comprises an outer plug configured to be positioned within the lumen of the at least one chamber and an inner plug configured to be positioned within the outer plug, and wherein the two-plug system extends along the lumen of the chamber; and
at least one seal configured to enclose either or both the proximal end and the distal end of the chamber.

* * * * *